United States Patent [19]
Hakamata

[11] Patent Number: 6,152,875
[45] Date of Patent: Nov. 28, 2000

[54] GLUCOSE CONCENTRATION MEASURING METHOD AND APPARATUS

[75] Inventor: Kazuo Hakamata, Kanagawa, Japan

[73] Assignee: Fuji Photo Film Co., Ltd., Kanagawa-Ken, Japan

[21] Appl. No.: 09/220,851

[22] Filed: Dec. 28, 1998

[30] Foreign Application Priority Data

Dec. 25, 1997 [JP] Japan ..................... 9-358101
Jul. 24, 1998 [JP] Japan .................... 10-209119

[51] Int. Cl.[7] ........................................ A61B 5/00
[52] U.S. Cl. ............................... 600/319; 600/316
[58] Field of Search .......................... 600/316, 318, 600/319, 322

[56] References Cited

U.S. PATENT DOCUMENTS

| 3,958,560 | 5/1976 | March . | |
|---|---|---|---|
| 4,895,159 | 1/1990 | Weiss | 600/316 |
| 5,433,197 | 7/1995 | Stark . | |
| 5,535,743 | 7/1996 | Backhaus et al. . | |
| 5,710,630 | 1/1998 | Essenpreis et al. | 600/316 |
| 5,835,215 | 11/1998 | Toida et al. | 600/319 |
| 5,961,449 | 10/1999 | Toida et al. | 600/319 |
| 5,969,815 | 10/1999 | Toida et al. | 600/316 |

FOREIGN PATENT DOCUMENTS

| 0 807 812 | 11/1997 | European Pat. Off. . |
|---|---|---|
| 6-503245 | 4/1994 | Japan . |
| 9-299333 | 11/1997 | Japan . |
| 9-512722 | 12/1997 | Japan . |

Primary Examiner—Eric F. Winakur
Assistant Examiner—Joseph A Cadugan
Attorney, Agent, or Firm—Sughrue, Mion, Zinn, Macpeak & Seas, PLLC

[57] ABSTRACT

A light beam, which has been radiated out of a predetermined light source, is irradiated to the eyeball lying at a predetermined position. Each of intensity values of first and second backward scattered light beams of the light beam having been irradiated to the eyeball is detected. The first backward scattered light beam comes from an interface between the cornea of the eyeball and the ambient air, and the second backward scattered light beam comes from an interface between the cornea and the anterior aqueous chamber of the eyeball. A refractive index of the aqueous humor, which fills the anterior aqueous chamber, is calculated from the intensity values of the first and second backward scattered light beams. A concentration of glucose in the aqueous humor is calculated in accordance with correlation between the refractive index of the aqueous humor and the concentration of glucose in the aqueous humor, which correlation has been found previously, and in accordance with the calculated refractive index of the aqueous humor.

48 Claims, 15 Drawing Sheets

GLUCOSE CONCENTRATION MEASURING METHOD AND APPARATUS

BACKGROUND OF THE INVENTION

1. Field of the Invention

This invention relates to a method and apparatus for measuring a concentration of glucose in a living body. This invention particularly relates to a method and apparatus for non-invasively measuring the concentration of glucose in the aqueous humor in the anterior aqueous chamber of the eyeball.

2. Description of the Prior Art

The mean level of glucose in the blood varies for different persons and is an important index for determining whether drugs are to be or are not to be administered to diabetic patients.

The concentration of glucose in the blood has the characteristics such that it fluctuates markedly within a very short time in accordance with food intake, physical activity, a complication by another disease, or the like. Urgent dosage is often required due to a sharp increase in concentration of blood glucose.

Therefore, as for patients having such a disease, it is desired that the concentration of glucose in the blood can be monitored at as short intervals as possible. Ordinarily, monitoring of the concentration of glucose in the blood is carried out by lancing the finger of the patient in order to obtain a drop of blood, analyzing the drop of blood, and thereby measuring the concentration of glucose in the blood. Since the lancing of the finger is painful, it is difficult to compel the patients to undergo the measurement procedure many times per day.

Accordingly, recently, in lieu of the invasive measurements having the drawbacks described above, various non-invasive measuring methods, which are not accompanied by pain, have been proposed.

The non-invasive measuring methods are primarily based upon the findings in that the concentration of glucose in the aqueous humor, which fills the anterior aqueous chamber located between the cornea and the crystalline lens of the human eyeball, has strong correlation with the concentration of glucose in the blood, though the level of correlation varies for different persons. With the non-invasive measuring methods, the concentration of glucose in the aqueous humor is measured non-invasively.

For example, a glucose sensor system, wherein the angle of rotation of infrared radiation having impinged upon the aqueous humor is measured, and the concentration of glucose having relationship with the angle of rotation is thereby determined, is proposed in, for example, U.S. Pat. No. 3,958,560. Also, a technique for measuring stimulated Raman light from glucose is disclosed in, for example, PCT Japanese Publication No. 6(1994)-503245.

Further, a device for measuring the optical properties of light reflected from the crystalline lens of the eye is described in, for example, Japanese Unexamined Patent Publication No. 6(1994)-237898. Furthermore, a method of measuring the concentration of glucose in the aqueous humor is described in, for example, U.S. Pat. No. 5,433,197.

Also, in U.S. Pat. No. 5,835,215 a method of measuring a concentration of glucose in the aqueous humor by measuring an absorbance of the aqueous humor was proposed. In the proposed method, a signal light beam is irradiated to the eyeball, and the intensity of the signal light beam reflected from an interface between the anterior aqueous chamber and the crystalline lens of the eyeball is detected. In this manner, the absorbance of the aqueous humor is measured. Since the light beam, which is reflected from an interface between the cornea and the anterior aqueous chamber, is mixed as noise in the reflected signal light beam, in the proposed method, a heterodyne detection technique is utilized in order to eliminate the noise, and the concentration of glucose in the aqueous humor is detected accurately.

However, with the device described in Japanese Unexamined Patent Publication No. 6(1994)-237898, light reflected from the interface between the cornea and the aqueous humor cannot be eliminated, and information representing absorption at the cornea is detected together with the necessary information. Therefore, the accuracy, with which the concentration of glucose in the aqueous humor is determined, cannot be kept high.

Further, in Japanese Unexamined Patent Publication No. 6(1994)-237898, nothing is disclosed as to technical means to be used for measuring a minute change in absorbance. Therefore, the device described in Japanese Unexamined Patent Publication No. 6(1994)-237898 cannot be appropriately used in practice.

The technique proposed in U.S. Pat. No. 3,958,560 has the problems in that polarization occurs at respective interfaces in the eyeball, and it is not possible to separate only the polarized light due to the aqueous humor.

With the technique disclosed in PCT Japanese Publication No. 6(1994)-503245, in order for stimulated Raman light from glucose to be measured, a pump laser beam having a high intensity is introduced into the anterior aqueous chamber and in a direction normal to the vision line optical axis. Therefore, a practical measuring system cannot be constituted easily.

With the techniques for calculating the concentration of glucose in accordance with optical characteristic values of the aqueous humor, such as the absorbance or the refractive index, which are proposed in, for example, U.S. Pat No. 5,835,215 and PCT Japanese Publication No. 9(1997)-512722, such that adverse effects of the constituents (e.g., NaCl) other than glucose, which are contained in the aqueous humor, upon the optical characteristic values, such as the absorbance or the refractive index, may be eliminated, it is necessary for the measurement to be repeated by using at least five kinds of light beams having different wavelengths. Also, it is necessary for a correction of the optical characteristic values, such as the absorbance or the refractive index, to be made due to a temperature difference between a deep portion and a hallow portion in the anterior aqueous chamber, through which a light beam passes. Therefore, the measurement and the information processing cannot be kept simple.

SUMMARY OF THE INVENTION

The primary object of the present invention is to provide a glucose concentration measuring method, wherein the concentration of glucose in the aqueous humor is measured non-invasively, with a high accuracy, and with a constitution simpler than with the conventional techniques.

Another object of the present invention is to provide an apparatus for carrying out the glucose concentration measuring method.

Extensive research has provided that there is a strong correlation between the concentration of glucose in the aqueous humor and the refractive index of the aqueous humor. The present invention is based upon such findings. In glucose concentration measuring methods and apparatuses in accordance with the present invention, a light beam is irradiated to the eyeball, and a refractive index of the aqueous humor, which fills the anterior aqueous chamber, is calculated from an intensity of the light beam reflected from the anterior aqueous chamber, or the like. Also, the concentration of glucose in the aqueous humor is non-invasively measured in accordance with the refractive index of the aqueous humor and correspondence relationship between the concentration of glucose in the aqueous humor and the refractive index of the aqueous humor, which relationship has been found experimentally. The glucose concentration measuring methods and apparatuses in accordance with the present invention vary from one another in how the refractive index of the aqueous humor is calculated.

DESCRIPTION OF THE PREFERRED EMBODIMENTS

The present invention will hereinbelow be described in further detail with reference to the accompanying drawings.

Figure 1:
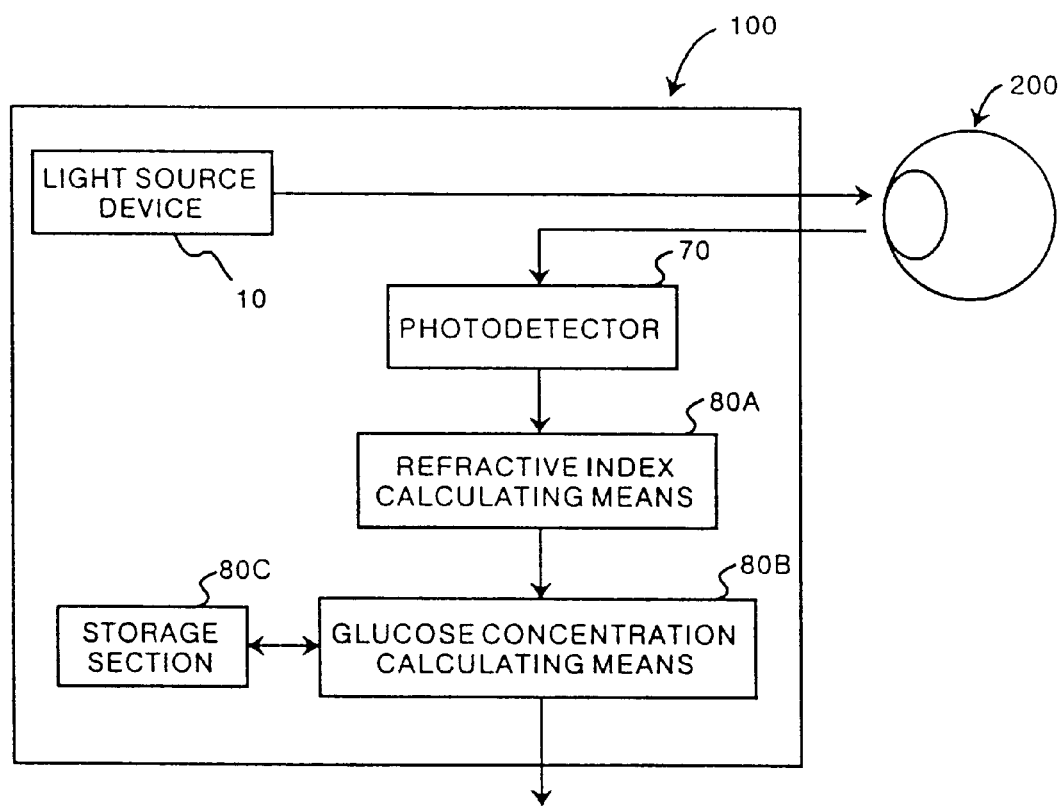
FIG. 1 is a block diagram showing a fundamental constitution of an apparatus for carrying out the first glucose concentration measuring method in accordance with the present invention.

FIG. 1 is a block diagram showing a fundamental constitution of an apparatus for carrying out the first glucose concentration measuring method in accordance with the present invention.

Figure 2:
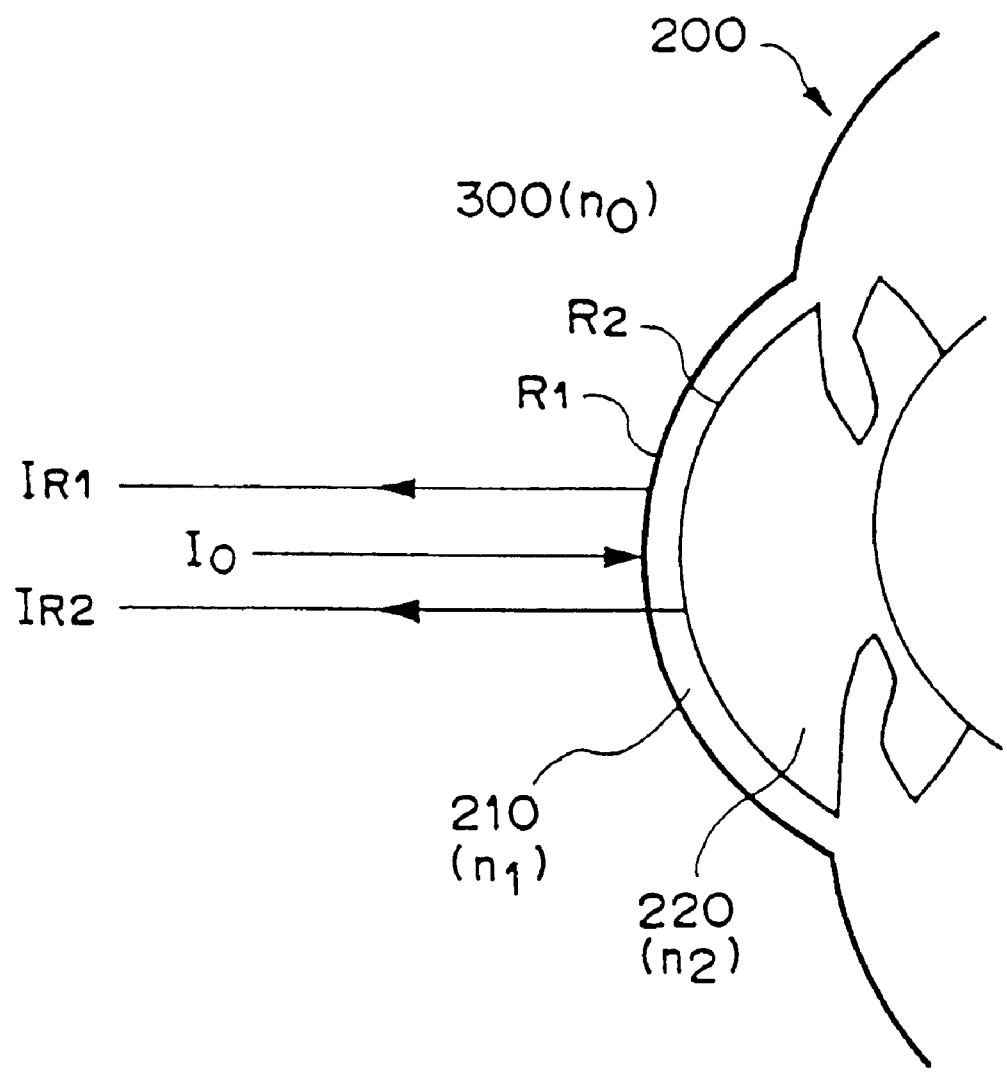
FIG. 2 is an explanatory view showing a relationship between an incident light beam impinging upon the eyeball and backward scattered light beams.

With reference to FIG. 1, a glucose concentration measuring apparatus 100 comprises a light source device 10 for irradiating a light beam (having an intensity $I_0$) to the eyeball 200 lying at a predetermined position. The glucose concentration measuring apparatus 100 also comprises a photodetector 70 for detecting each of an intensity $I_{R1}$ of a first backward scattered light beam of the light beam, which has been radiated out of the light source device 10 and irradiated to the eyeball 200, the first backward scattered light beam being the reflected light beam coming from an interface $R_1$ between the cornea 210 of the eyeball 200 and the ambient air 300 around the eyeball 200 (as illustrated in FIG. 2), and an intensity $I_{R2}$ of a second backward scattered light beam of the light beam, which has been radiated out of the light source device 10 and irradiated to the eyeball 200, the second backward scattered light beam being the reflected light beam coming from an interface $R_2$ between the cornea 210 and the anterior aqueous chamber 220 of the eyeball 200. The glucose concentration measuring apparatus 100 further comprises a refractive index calculating means 80A for calculating a refractive index $n_2$ of the aqueous humor, which fills the anterior aqueous chamber 220, from the intensity $I_{R1}$ of the first backward scattered light beam and the intensity $I_{R2}$ of the second backward scattered light beam. The glucose concentration measuring apparatus 100 still further comprises a storage section 80C, in which the information representing correspondence relationship between the refractive index $n_2$ of the aqueous humor and a concentration G of glucose in the aqueous humor has been stored previously. The glucose concentration measuring apparatus 100 also comprises a glucose concentration calculating means 80B for calculating a concentration G of glucose in the aqueous humor in accordance with the correspondence relationship, which has been stored in the storage section 80C, and the refractive index $n_2$ of the aqueous humor, which has been calculated by the refractive index calculating means 80A.

In the glucose concentration measuring apparatus 100 (and those which will be described later), the correspondence relationship between the refractive index $n_2$ of the aqueous humor and the concentration G of glucose in the aqueous humor, which relationship has been stored in the storage section 80C, may be stored as a table or as a function, such as a regression formula.

How the refractive index $n_2$ of the aqueous humor is calculated from the intensity $I_{R1}$ of the first backward scattered light beam and the intensity $I_{R2}$ of the second backward scattered light beam in the refractive index calculating means 80A will be described hereinbelow.

FIG. 2 is an explanatory view showing the relationship between the incident light beam impinging upon the eyeball 200 and the backward scattered light beams.

The refractive index of ambient air 300 around the eyeball 200 with respect to the incident light beam impinging upon the eyeball 200 may be represented by $n_0$, and the refractive index of the cornea 210 may be represented by $n_1$. In such cases, the intensity $I_{R1}$ of the light beam (i.e., the first backward scattered light beam) having been reflected front the interface $R_1$ between the cornea 210 and the ambient air 300 may be represented by Formula (1) shown below.

$$I_{R1}=I_I\{(n_0-n_1)/(n_0+n_1)\}^2 \tag{1}$$

Also, the value of $\{(n_0-n_1)/(n_0+n_1)\}^2$ may be represented as a reflectivity R1, and the intensity of the light: beam (i.e., the second backward scattered light beam) having been reflected from the interface $R_2$ between the cornea 210 and the anterior aqueous chamber 220 may be represented by $I_{R2}$. The absorbance of the cornea 210 may be represented by a, the thickness of the cornea 210 may be represented by d, and the refractive index of the aqueous humor, which fills the anterior aqueous chamber 220, may be represented by $n_2$. In such cases, Formula (2) shown below obtains.

$$I_{R2}=I_0(1-R1)^2 10^{-2ad}\{(n_1-n_2)/(n_1+n_2)\}^2 \tag{2}$$

From Formula (2) and a substitution of $k=(I_{R2}/I_0)$, the refractive index $n_2$ of the aqueous humor can be calculated with Formula (3) or Formula (4) shown below.

$$n_2=(-2kn_1-2n_1+4k^{1/2}n_1)/\{2(k-1)\} \tag{3}$$

$$n_2=(-2kn_1-2n_1 4k^{1/2}n_1)/\{2(k-1)\} \tag{4}$$

As the solutions of the refractive index $n_2$, two kinds of solutions represented by Formulas (3) and (4) are obtained. It was found that the value represented by Formula (3) matches with the results of experiments.

The technique for calculating the refractive index $n_2$ in this manner is also applicable to the embodiments, which will be described later.

Figure 3:
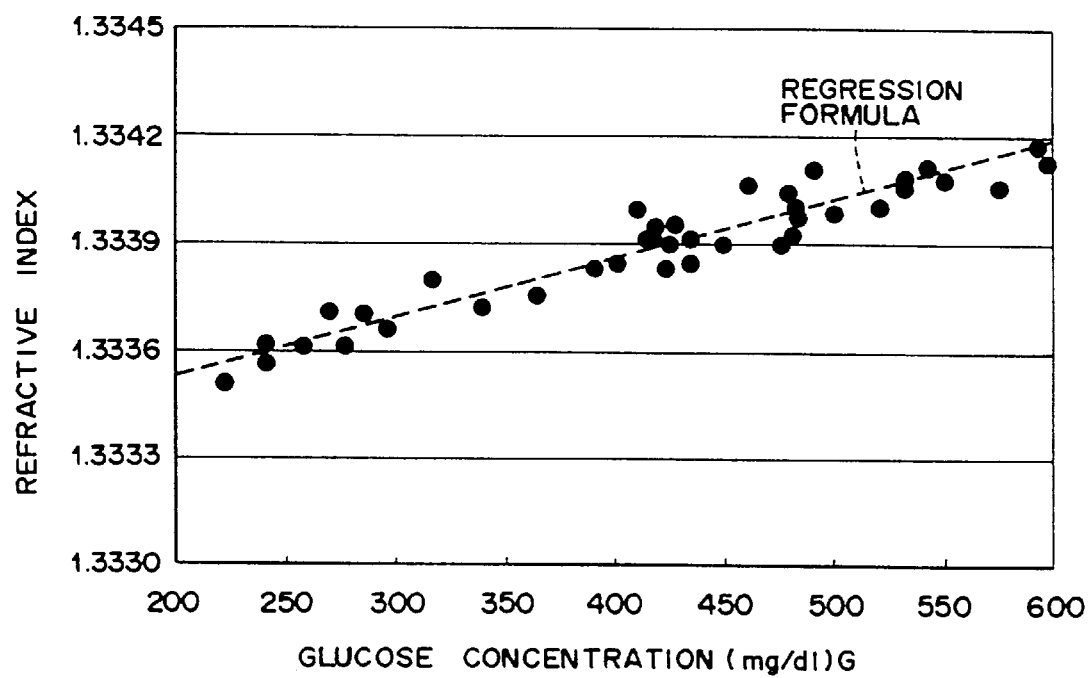
FIG. 3 is a graph showing a correlation between a refractive index of the aqueous humor and a concentration of glucose in the aqueous humor.

As the correlation between the refractive index $n_2$ of the aqueous humor and the concentration G of glucose in the aqueous humor, which correlation is stored in the storage section 80C, for example, the correlation shown in FIG. 3 may be employed. The correlation shown in FIG. 3 may be typically represented by the regression formula shown below.

$$n_2=1.33322+1.6\times10^{-6}\times G$$

The glucose concentration calculating means 80B calculates the concentration G of glucose in the aqueous humor in accordance with the correlation between the refractive index $n_2$ of the aqueous humor and the concentration G of glucose in the aqueous humor, which correlation has been stored in the storage section 80C, and the refractive index $n_2$ of the aqueous humor, which has been calculated by the refractive index calculating means 80A.

In this manner, with the glucose concentration measuring apparatus 100, the concentration of glucose in the aqueous humor can be measured non-invasively, with a high accuracy, and with the constitution simpler than with the conventional techniques.

With the conventional technique wherein the concentration of glucose is measured by measuring the absorbance of the aqueous humor, such that measurement error due to the presence of many kinds of constituents, which absorb the incident light beam, in the aqueous humor, it is necessary for the measurement to be repeated by using a plurality of kinds (ordinarily, at least five kinds) of light beams having different wavelengths. However, with this embodiment of the glucose concentration measuring apparatus in accordance with the present invention, wherein the correspondence relationship between the refractive index with respect to one kind of light beam having a predetermined wavelength and the concentration of glucose is utilized, the measurement can be carried out by using only the light beam having the predetermined wavelength, and the time required to carry out the measurement can be kept markedly short.

This embodiment of the glucose concentration measuring apparatus in accordance with the present invention may further comprise an aqueous humor glucose concentration-to-blood glucose concentration converting means. For each patient, the correlation between the concentrations of glucose in the aqueous humor, which have thus been obtained with the glucose concentration measuring apparatus in accordance with the present invention, and the concentrations of glucose in the blood, which have been obtained invasively in accordance with the conventional procedure, may be prepared as, for example, a conversion table. The information representing the conversion table may be stored in the aqueous humor glucose concentration-to-blood glucose concentration converting means. When information representing the concentration of glucose in the aqueous humor of a certain patient is fed from the glucose concentration measuring apparatus described above into the aqueous humor glucose concentration-to-blood glucose concentration converting means, reference may be made to the aquecus humor glucose concentration-to-blood glucose concentration conversion table, which corresponds to the patient, and the concentration of glucose in the blood can thereby be calculated. Accordingly, the concentration of glucose in the blood can be determined non-invasively.

In the embodiments, which will be described later, the aqueous humor glucose concentration-to-blood glucose concentration converting means may be provided, and the same effects as those described above can thereby be obtained.

Figure 4:
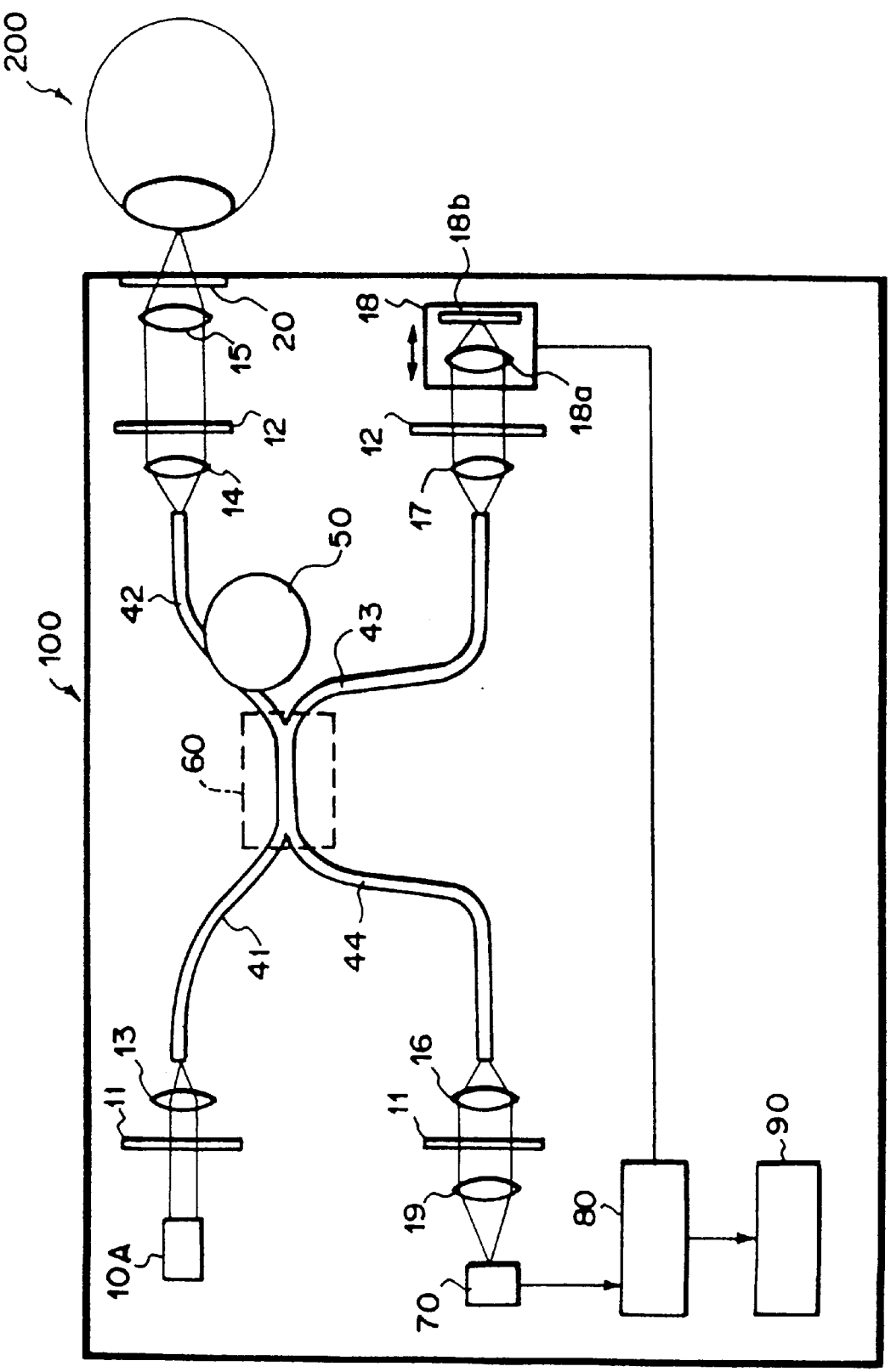
FIG. 4 is a schematic view showing an embodiment of the glucose concentration measuring apparatus for carrying out the second glucose concentration measuring method in accordance with the present invention.

FIG. 4 is a schematic view showing an embodiment of the glucose concentration measuring apparatus for carrying out the second glucose concentration measuring method in accordance with the present invention. The embodiment of FIG. 4 more specifically embodies the glucose concentration measuring apparatus of FIG. 1 with respect to the technique for obtaining the intensity $I_{R1}$ of the first backward scattered light beam and the intensity $I_{R2}$ of the second backward scattered light beam.

With reference to FIG. 4, the glucose concentration measuring apparatus 100 comprises a light source device 10A (e.g., an SLD) for radiating out a low coherence light beam having a coherence length of approximately several tens of microns. The glucose concentration measuring apparatus 100 also comprises a half-wave plate 11 for converting the low coherence light beam, which has been radiated out of the light source device 10A, into a linearly polarized light beam, and a converging lens 13 for converging the linearly polarized light beam. The glucose concentration measuring apparatus 100 further comprises first to fourth polarization plane keeping fibers 41, 42, 43, 44 for transferring the light beam, which has entered from an entry end, to a radiating end such that the plane of polarization of the incident light beam may be kept, and a polarization plane keeping coupler 60 for transferring the light beam, which has been received from each polarization plane keeping fiber, to a different polarization plane keeping fiber such that the plane of polarization of the incident light beam may be kept. The glucose concentration measuring apparatus 100 still further comprises a modulator 50 for modulating the frequency of the light beam (i.e., an irradiated light beam), which is guided through the second polarization plane keeping fiber 42 for guiding the light beam to the eyeball 200, by, for example, 1 Hz. (The modulation frequency is not limited to 1 Hz.) The glucose concentration measuring apparatus 100 also comprises a lens 14 for collimating the irradiated light beam, which has been radiated out of the second polarization plane keeping fiber 42, and a quarter-wave plate 12 for converting the collimated light beam into a circularly polarized light beam. The glucose concentration measuring apparatus 100 further comprises a converging lens 15 for converging the circularly polarized light beam onto the interfaces $R_1$ and $R_2$ in the eyeball 200 (as illustrated in FIG. 2), and an external light cut-off filter 20 for transmitting only the reflected light beams coming from the eyeball 200 (i.e., only the first backward scattered light beam, which is the reflected light beam coming from the interface $R_1$ between the cornea 210 and the ambient air 300, and the second backward scattered light beam, which is the reflected light beam coming from the interface $R_2$ between the cornea 210 and the anterior aqueous chamber 220). The glucose concentration measuring apparatus 100 still further comprises a lens 17 for collimating the light beam (i.e., a reference light beam), which has been transferred by the polarization plane keeping coupler 60 from the first polarization plane keeping fiber 41 to the third polarization plane keeping fiber 43, and a quarter-wave plate 12 for converting the collimated light beam into a circularly polarized light beam. The glucose concentration measuring apparatus 100 also comprises a reference mirror unit 18, which is provided with a reference mirror 18b and a converging lens 18a and is capable of moving along the optical axis direction. The glucose concentration measuring apparatus 100 further comprises a lens 16 for collimating the light beam, which returns from the second polarization plane keeping fiber 42 and serves a signal light beam (i.e., each of the first and second backward scattered light beams), and the reference light beam, which returns from the third polarization plane keeping fiber 43, at the radiating end of the fourth polarization plane keeping fiber 44. The glucose concentration measuring apparatus 100 still further comprises a half-wave plate 11 for rotating the direction of polarization by an angle of 90 degrees, and a converging lens 19 for converging the light beam, which comes from the half-wave plate 11, onto a photodetector 70. The glucose concentration measuring apparatus 100 also comprises the photodetector 70 for detecting the intensity of the light beam having been converged by the converging lens 19. The glucose concentration measuring apparatus 100 further comprises a signal processing circuit 80 for calculating the refractive index $n_2$ of the aqueous humor, which fills the anterior aqueous chamber 220 of the eyeball 200, from the intensity of the light beam, which has been detected by the photoddetector 70, and calculating the concentration G of glucose in the aqueous humor in accordance with the calculated refractive index $n_2$ of the aqueous humor and the correlation between the refractive index $n_2$ of the aqueous humor and the concentration G of glucose in the aqueous humor, which correlation has been stored in the signal processing circuit 80. The glucose concentration measuring apparatus 100 still further comprises a display device 90 for displaying the calculated concentration G of glucose in the aqueous humor.

The signal processing circuit 80 has the functions for the refractive index calculating means, the glucose concentration calculating means, and the storage section.

How the glucose concentration measuring apparatus 100 of FIG. 4 operates will be described hereinbelow.

Firstly, the low coherence light beam is radiated out of the light source device 10A. The low coherence light beam is converted by the half-wave plate 11 into the linearly polarized light beam, and the linearly polarized light beam is converged by the converging lens 13 and is caused to enter into the first polarization plane keeping fiber 41. The linearly polarized light beam is guided through the first polarization plane keeping fiber 41 and is then caused by the polarization plane keeping coupler 60 to enter into the second and third polarization plane keeping fibers 42 and 43 such that the plane of polarization of the linearly polarized light beam may be kept. The frequency of the light beam, which travels through the second polarization plane keeping fiber 42, is shifted by, for example, 1 Hz, by the modulator 50. The light beam is then radiated out of the second polarization plane keeping fiber 42 and collimated by the lens 14. Thereafter, the collimated light beam is converted by the quarter-wave plate 12 into the circularly polarized light beam and converged by the converging lens 15 onto the interfaces $R_1$ and $R_2$ in the eyeball 200 (as illustrated in FIG. 2). At this time, the intensity of the light. beam impinging upon the eyeball 200 is adjusted to be equal to $I_0$.

The light beam, which has impinged upon the eyeball 200, is reflected from the interfaces $R_1$ and $R_2$. The first backward scattered light beam, which has been reflected from the interface $R_1$, and the second backward scattered light beam, which has been reflected from the interface $R_2$, pass through the external light cut-off filter 20, the converging lens 15, the quarter-wave plate 12, and the lens 14 and then enter into the second polarization plane keeping fiber 42.

Since the first and second backward scattered light beams, which have entered into the second polarization plane keeping fiber 42, have passed through the quarter-wave plate 12, they have a plane of polarization having been rotated by an angle of 90 degrees with respect to the original plane of polarization. The first and second backward scattered light beams enter into the polarization plane keeping coupler 60.

The reference light beam, which has been separated by the polarization plane keeping coupler 60 and entered into the third polarization plane keeping fiber 43, is collimated by the lens 17, converted by the quarter-wave plate 12 into the circularly polarized light beam, and reflected by the reference mirror unit 18. The reference light beam then passes through the quarter-wave plate 12 and the lens 17, enters into the third polarization plane keeping fiber 43, and is guided to the polarization plane keeping coupler 60.

The first and second backward scattered light beams and the reference light beam, which have been guided to the polarization plane keeping coupler 60, are caused to enter into the fourth polarization plane keeping fiber 44, pass through the lens 16, the half-wave plate 11, and the converging lens 19, and impinge upon the photodetector 70.

The first or second backward scattered light beam, which has returned from the second polarization plane keeping fiber 42 and entered into the polarization plane keeping coupler 60, and the reference light beam, which has returned from the third polarization plane keeping fiber 43 and entered into the polarization plane keeping coupler 60, have the planes of polarization coinciding with each other, and can therefore interfere with each other. However, the planes of polarization of the first or second backward scattered light beam and the reference light beam do not coincide with the plane of polarization of the light beam, which has entered from the first polarization plane keeping fiber 41 into the polarization plane keeping coupler 60. Therefore, the first or second backward scattered light beam and the reference light beam cannot interfere with the light beam, which has entered from the first polarization plane keeping fiber 41 into the polarization plane keeping coupler 60.

The first or second backward scattered light beam and the reference light beam, which has returned from the third polarization plane keeping fiber 43, interfere with each other when their optical path lengths coincide with each other. The first backward scattered light beam and the second backward scattered light beam have a difference in optical path length, which difference is equal to two times as long as the thickness of the cornea 210. Therefore, by the movement of the reference mirror unit 18 along the optical axis direction, only either one of the first backward scattered light beam and the second backward scattered light beam can be selectively caused to interfere with the reference light beam. Also, the thickness of the cornea 210 can be measured accurately by measuring the distance between the position, at which the reference mirror unit 18 was located when the interference light beam occurring from the interference of the first backward scattered light beam and the reference light beam with each other was observed, and the position, at which the reference mirror unit 18 was located when the interference light beam occurring from the interference of the second backward scattered light beam and the reference light beam with each other was observed.

When the first or second backward scattered light beam and the reference light beam, which has returned from the third polarization plane keeping fiber 43, interfere with each other, a beat signal occurs, the intensity of which repeatedly becomes high and low at a frequency equal to the difference in frequency (in this case, 1 Hz) between the backward scattered light beam and the reference light beam interfering with each other. The intensity of the beat signal is detected by the photodetector 70, and the intensity of the corresponding backward scattered light beam is calculated with the optical heterodyne detection processing. Also, the reference mirror unit 18 is moved, and the other backward scattered light beam is caused to interfere with the reference light beam. The intensity of the beat signal having thus been caused to occur is detected by the photodetector 70, and the intensity of the other backward scattered light beam can thus be calculated with the optical heterodyne detection processing.

The signal processing circuit 80 calculates the refractive index $n_2$ of the aqueous humor with the formula shown above and in accordance with the thus calculated intensity $I_{R1}$ of the first backward scattered light beam, the intensity $I_{R2}$ of the second backward scattered light beam, the thickness d of the cornea 210, which may be found from the distance of movement of the reference mirror unit 18, the already known refractive indexes $n_0$ and $n_1$, the reflectivity R1, and the absorbance a of the cornea 210. Also, the signal processing circuit 80 calculates the concentration G of glucose in the aqueous humor of the eyeball, which is subjected to the measurement, in accordance with the calculated refractive index $n_2$ of the aqueous humor and the correlation between the refractive index $n_2$ of the aqueous humor and the concentration G of glucose in the aqueous humor, which correlation has been stored in the signal processing circuit 80. The information representing the results of the calculation is fed from the signal processing circuit 80 into the display device 90.

The display device 90 displays the concentration G of glucose represented by the received information.

In this manner, with the glucose concentration measuring apparatus 100 of FIG. 4, the weak reflected light beams coming from the eyeball can be detected accurately with the optical heterodyne detection processing. Also, the concentration of glucose in the aqueous humor can be measured non-invasively and with the constitution simpler than with the conventional techniques.

With the conventional technique wherein the concentration of glucose is measured by measuring the absorbance of the aqueous humor, such that measurement error due to the presence of many kinds of constituents, which absorb the incident light beam, in the aqueous humor, it is necessary for the measurement to be repeated by using a plurality of kinds (ordinarily, at least five kinds) of light beams having different wavelengths. However, with this embodiment of the glucose concentration measuring apparatus 100 in accordance with the present invention, wherein the correspondence relationship between the refractive index with respect to one kind of light beam having a predetermined wavelength and the concentration of glucose is utilized, the measurement can be carried out by using only the light beam having the predetermined wavelength, and the time required to carry out the measurement can be kept markedly short.

Figure 5:
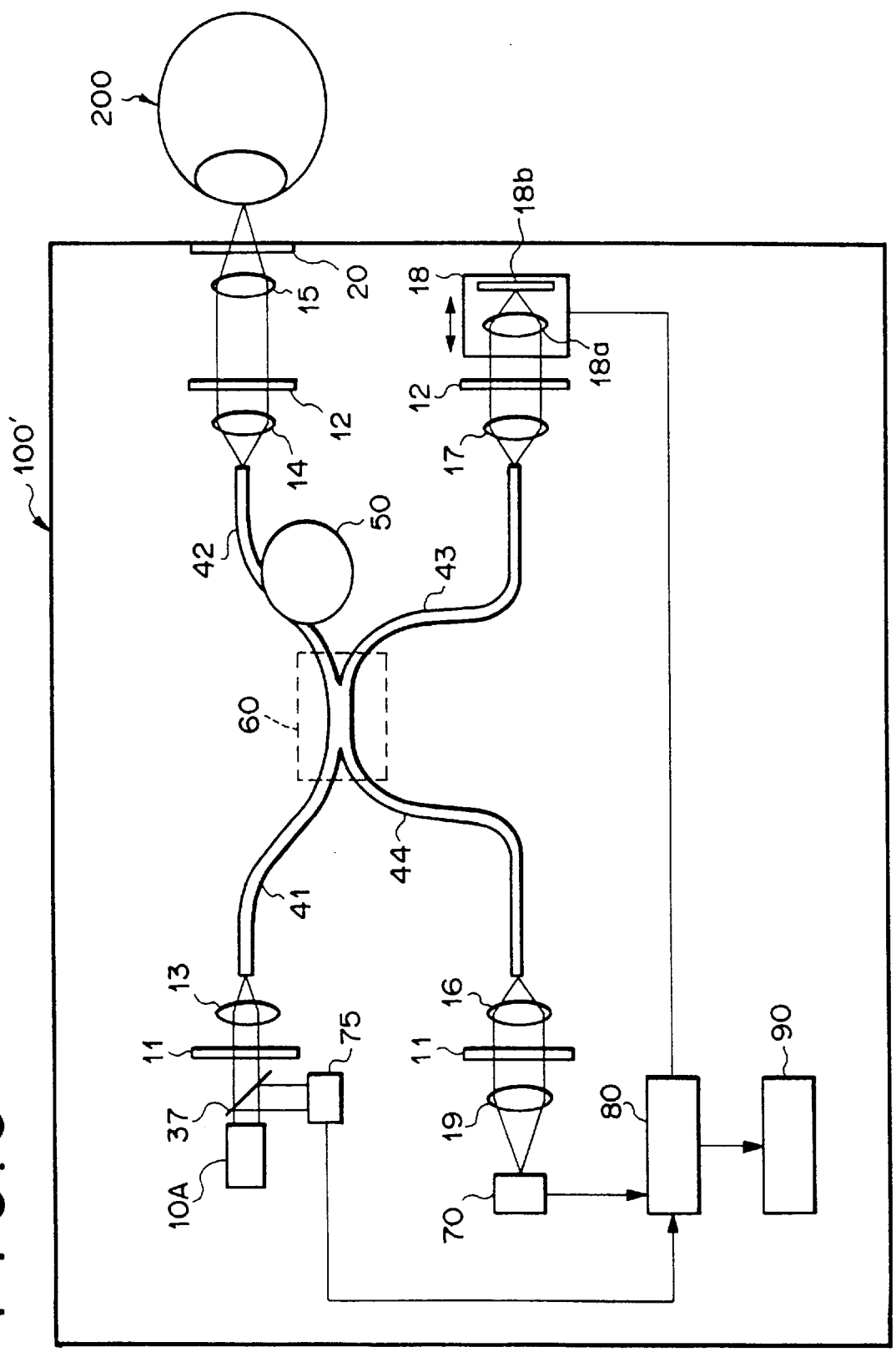
FIG. 5 is a schematic view showing a different embodiment of the glucose concentration measuring apparatus for carrying out the second glucose concentration measuring method in accordance with the present invention.

FIG. 5 is a schematic view showing a different embodiment of the glucose concentration measuring apparatus for carrying out the second glucose concentration measuring method in accordance with the present invention. A glucose concentration measuring apparatus 100' illustrated in FIG. the same has the glucose concentration measuring apparatus 100 shown in FIG. 4, except that the light source device 10A is a semiconductor laser (an SLD), an ND filter 37 is located between the SLD 10A and the half-wave plate 11, and a second photodetector 75 is provided. The ND filter 37 is inclined by an angle of approximately 45 degrees with respect to a plane, which is normal to the direction of travel of a laser beam having been radiated out of the SLD 10A. The second photodetector 75 detects the intensity of the laser beam having been reflected from the ND filter 37.

The SLD 10A radiates out a laser beam, which has wavelengths falling in the visible region (<1,400 nm), with an output power of 3 mW to 4 mW. The OD value of the ND filter 37 is set to be 3 to 4. Of the laser beam having been radiated out of the SLD 10A, the ND filter 37 transmits only the portion of approximately several microwatts and reflects the remaining major portion of the laser beam toward the direction, which intersects approximately perpendicularly to the direction of travel of the laser beam. Therefore, the laser beam of several microwatts impinges upon the eyeball 200. The value of several microwatts is smaller than the MPE value (JIS C-6802: the value defining a laser beam intensity of ⅒ of the level, which yields an injury occurrence rate of 50% due to laser beam irradiation), which is allowed to impinge upon the eyes. The remaining major portion of the laser beam, which has been reflected from the ND filter 37, impinges upon the second photodetector 75. The second photodetector 75 detects the intensity of the incident laser beam and feeds the information, which represents the detected intensity of the incident laser beam, into the signal processing circuit 80. The signal processing circuit 80 calculates the intensity $I_0$ of the laser beam, which impinges upon the eyeball 200, from the received information, which represents the intensity of the laser beam, and the OD value of the ND filter 37. The calculated intensity $I_0$ of the laser beam, which impinges upon the eyeball 200, is used in the calculation of the refractive index of the aqueous humor.

Also, the ND filter 37 reflects large portions of return light beams, which return through the first polarization plane keeping fiber 41 toward the SLD 10A, such as the interference light beams occurring from the interference of the first and second backward scattered light beams and the reference light beam with each other. Therefore, the return light beams do not impinge upon the SLD 10A. Accordingly, the return light beams (the reference light beam, and the like) traveling toward the SLD 10A can be obstructed from impinging upon the SLD IOA, and the intensity of the laser beam radiated out of the SLD 10A can be prevented from becoming unstable due to the impingement of the return light beams. As a result, with the glucose concentration measuring apparatus 100' of FIG. 5, the laser beam having a stable intensity can be irradiated to the eyeball 200, the intensity of each backward scattered light beam coming from the eyeball 200 can be kept stable, and the accuracy, with which each backward. scattered light beam is measured, can be kept high.

In the glucose concentration measuring apparatus 100' of FIG. 5, the second photodetector 75 is located such that its light receiving face may be normal to the direction of travel of the laser beam having been reflected from the ND filter 37. With such orientation of the second photodetector 75, there is the risk that the incident laser beam will be reflected by the light receiving face of the second photodetector 75, and the thus reflected laser beam will travel reversely along the optical path of the incident laser beam and will return to the SLD 10A.

Figure 6:
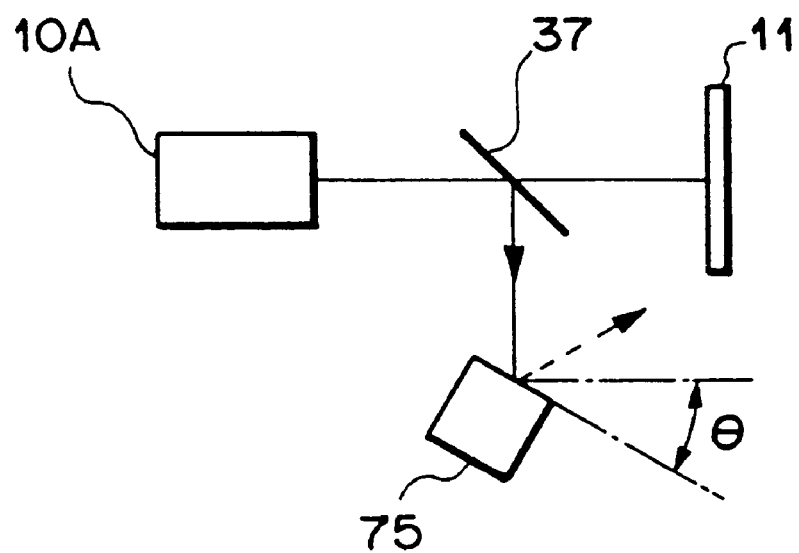
FIG. 6 is a schematic view showing an appropriate example of orientation of a second photodetector in the glucose concentration measuring apparatus shown in FIG. 5.

Therefore, as illustrated in FIG. 6, such that the laser beam reflected from the second photodetector 75 may not return to the SLD 10A, instead of being located such that the light receiving face may be normal to the direction of travel of the incident laser beam, the second photodetector 75 should preferably be located such that its light receiving face may be inclined by an angle θ with respect to the plane, which is normal to the direction of travel of the incident laser beam.

Figure 7:
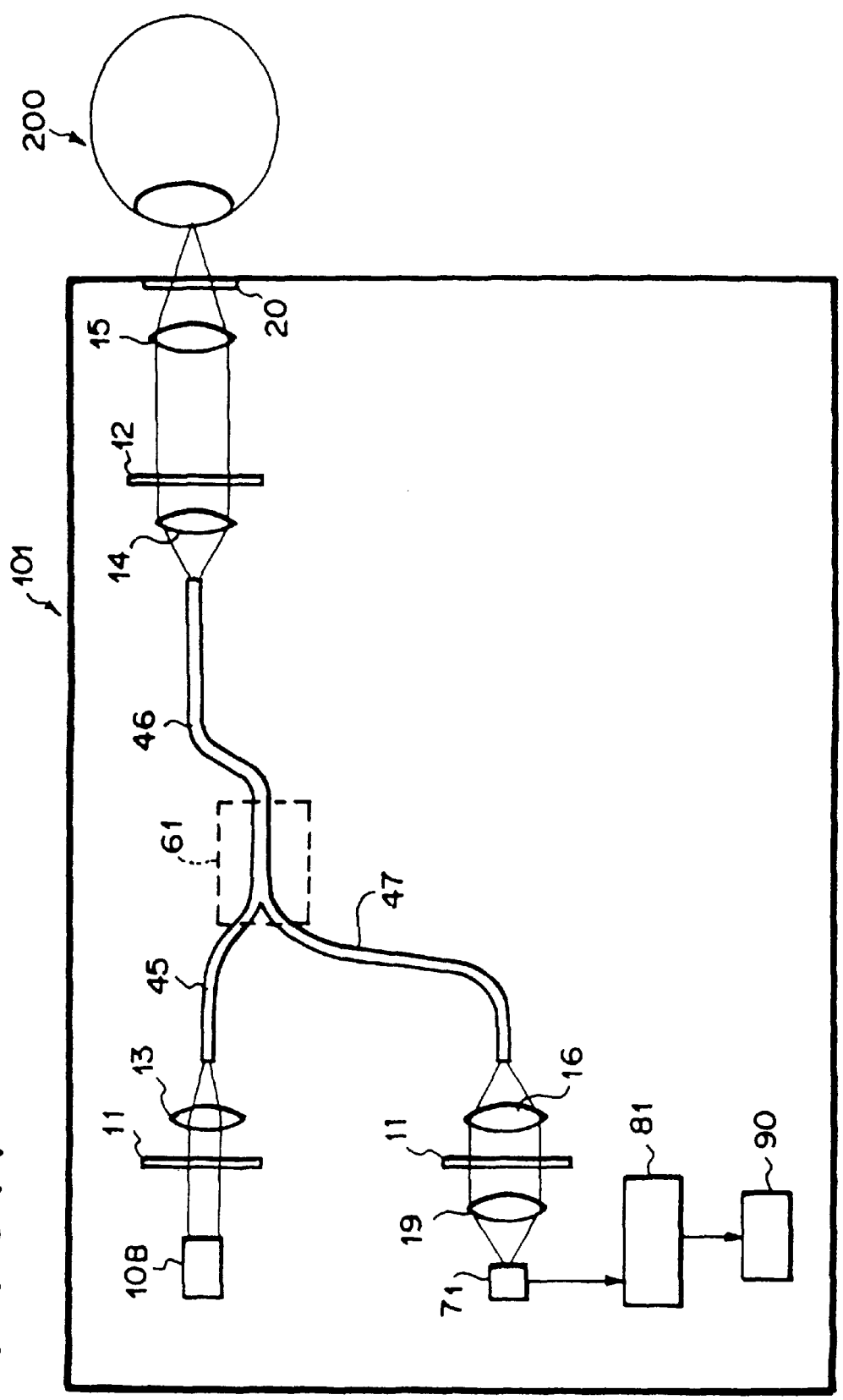
FIG. 7 is a schematic view showing an embodiment of the glucose concentration measuring apparatus for carrying out the third glucose concentration measuring method in accordance with the present invention.

FIG. 7 is a schematic view showing an embodiment of the glucose concentration measuring apparatus for carrying out the third glucose concentration measuring method in accordance with the present invention. The embodiment of FIG. 7 more specifically embodies the glucose concentration measuring apparatus of FIG. 1 with respect to the technique for obtaining the intensity $I_{R1}$ of the first backward scattered light beam and the intensity $I_{R2}$ of the second backward scattered light beam.

With reference to FIG. 7, a glucose concentration measuring apparatus 101 comprises a frequency-sweep laser beam source device 10B for producing a laser beam, whose frequency is swept temporally in a sawtooth-like form with a predetermined band. The glucose concentration measuring apparatus 101 also comprises the half-wave plate 11 for converting the laser beam, which has been radiated out of the laser beam source device 10B and the frequency of which is swept, into a linearly polarized light beam, and the converging lens 13 for converging the linearly polarized light beam. The glucose concentration measuring apparatus 101 further comprises first to third polarization plane keeping fibers 45, 46, 47, for transferring the light beam (the laser beam), which has entered from an entry end, to a radiating end such that the plane of polarization of the incident light beam may be kept, and a polarization plane keeping coupler 61 for transferring the light beam, which has been received from each polarization plane keeping fiber, to a different polarization plane keeping fiber such that the plane of polarization of the incident light beam may be kept. The glucose concentration measuring apparatus 101 still further comprises the lens 14 for collimating the irradiated light beam, which has been radiated out of the second polarization plane keeping fiber 46, and the quarter-wave plate 12 for converting the collimated light beam into a circularly polarized light beam. The glucose concentration measuring apparatus 101 also comprises the converging lens 15 for converging the circularly polarized light beam onto the interfaces $R_1$ and $R_2$ in the eyeball 200 (as illustrated in FIG. 2), and the external light cut-off filter 20 for transmitting only the reflected light beams coming from the eyeball 200 (i.e., only the first backward scattered light beam, which is the reflected light beam coming from the interface $R_1$ between the cornea 210 and the ambient air 300, and the second backward scattered light beam, which is the reflected light beam coming from the interface $R_2$ between the cornea 210 and the anterior aqueous chamber 220). The glucose concentration measuring apparatus 101 further comprises the lens 16 for collimating the light beam, which returns from the second polarization plane keeping fiber 46 and serves a signal light beam (i.e., each of the first and second backward scattered light beams), and the reference light beam, which is reflected from the quarter-wave plate 12 and returns from the second polarization plane keeping fiber 46, at the radiating end of the third polarization plane keeping fiber 47. The glucose concentration measuring apparatus 101 still further comprises the half-wave plate 11 for rotating the direction of polarization by an angle of 90 degrees, and the converging lens 19 for converging the light beam, which comes from the half-wave plate 11, onto a photodetector 71. The glucose concentration measuring apparatus 101 also comprises the photodetector 71 for detecting the intensity of the light beam having been converged by the converging lens 19. The glucose concentration measuring apparatus 101 further comprises a signal processing circuit 81 for calculating the refractive index $n_2$ of the aqueous humor, which fills the anterior aqueous chamber 220 of the eyeball 200, from the intensity of the light beam, which has been detected by the photodetector 71, and calculating the concentration G of glucose in the aqueous humor in accordance with the calculated refractive index $n_2$ of the aqueous humor and the correlation between the refractive index $n_2$ of the aqueous humor and the concentration G of glucose in the aqueous humor, which correlation has been stored in the signal processing circuit 81. The glucose concentration measuring apparatus 101 still further comprises the display device 90 for displaying the calculated concentration G of glucose in the aqueous humor.

The signal processing circuit 81 has the functions for the refractive index calculating means, the glucose concentration calculating means, and the storage section.

How the glucose concentration measuring apparatus 101 of FIG. 7 operates will be described hereinbelow.

Figure 8:
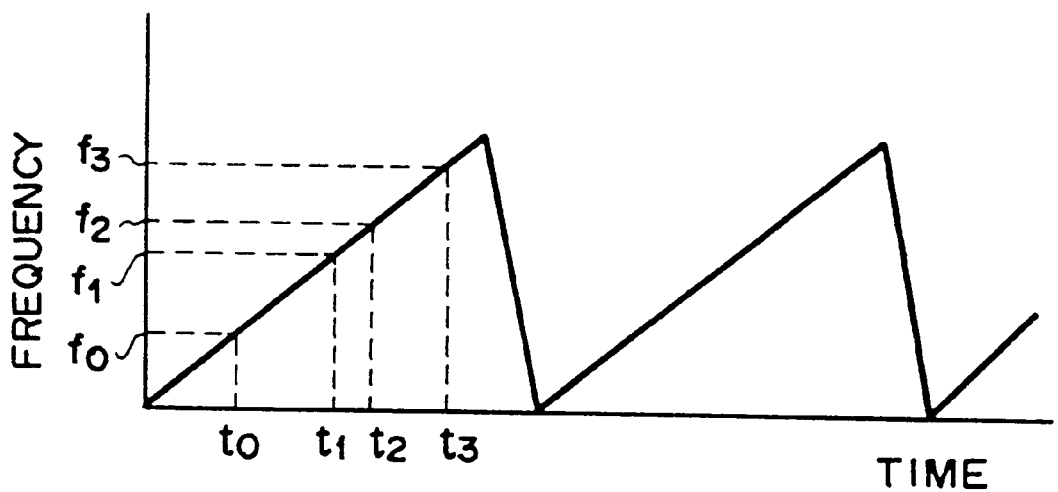
FIG. 8 is a graph showing a frequency sweeping pattern.

Firstly, the laser beam is radiated out of the frequency-sweep laser beam source device 10B. The frequency of the laser beam is swept on the time axis. As illustrated in FIG. 8, the frequency of the laser beam, which is radiated out of the frequency-sweep laser beam source device 10B at the time $t_0$, is represented by $f_0$.

The light beam (the laser beam) having the frequency $f_0$, which has been radiated out of the frequency-sweep laser beam source device 10B, is converted by the half-wave plate 11 into the linearly polarized light beam, and the linearly polarized light beam is converged by the converging lens 13 and is caused to enter into the first polarization plane keeping fiber 45. The linearly polarized light beam is guided through the first polarization plane keeping fiber 45 and is then caused by the polarization plane keeping coupler 61 to enter into the second polarization plane keeping fiber 46 such that the plane of polarization of the linearly polarized light beam may be kept. The light beam, which travels through the second polarization plane keeping fiber 46, is radiated out of a radiating end of the second polarization plane keeping fiber 46 and collimated by the lens 14. Thereafter, the collimated light beam is converted by the quarter-wave plate 12 into the circularly polarized light beam and converged by the converging lens 15 onto the interfaces $R_1$ and $R_2$ in the eyeball 200. At this time, the intensity of the light beam impinging upon the eyeball 200 is adjusted to be equal to $I_0$.

The light beam, which has impinged upon the eyeball 200, is reflected from the interfaces $R_1$ and $R_2$. The first backward scattered light beam, which has been reflected from the interface $R_1$, and the second backward scattered light beam, which has been reflected from the interface $R_2$, pass through the external light cut-off filter 20, the converging lens the quarter-wave plate 12, and the lens 14 and then enter into the second polarization plane keeping fiber 46.

Since the first and second backward scattered light beams, which have entered into the second polarization plane keeping fiber 46, have passed through the quarter-wave plate 12, they have a plane of polarization having been rotated by an angle of 90 degrees with respect to the original plane of polarization. The first and second backward scattered light beams enter into the polarization plane keeping coupler 61.

A portion of the light beam, which has been radiated out of the radiating end of the second polarization plane keeping fiber 46, is reflected from the quarter-wave plate 12 and again enters into the second polarization plane keeping fiber 46. The portion of the light beam serves as the reference light beam and enters into the polarization plane keeping coupler 61.

The first and second backward scattered light beams, which have impinged upon the eyeball 200 and reflected from it, respectively have differences in optical path length with respect to the reference light beam, which has been reflected from the quarter-wave plate 12. Specifically, the optical path length of the first backward scattered light beam is longer than the optical path length of the reference light beam by two times the distance from the quarter-wave plate 12 to the interface $R_1$. Also, the optical path length of the second backward scattered light beam is longer than the optical path length of the reference light beam by two times the distance from the quarter-wave plate 12 to the interface $R_2$.

Specifically, the first backward scattered light beam meets with the reference light beam at the quarter-wave plate 12 with an earlier timing than the second backward scattered light beam does. The difference in time between when the first backward scattered light beam meets with the reference light beam and when the second backward scattered light beam meets with the reference light beam depends upon the distance equal to two times the thickness of the cornea 210.

The laser beam, the frequency of which is swept temporally, is successively radiated out of the frequency-sweep laser beam source device 10B and successively arrives at the quarter-wave plate 12.

As a result, at the quarter-wave plate 12, the first backward scattered light beam (having the frequency $f_0$) of the laser beam, which has been radiated out of the laser beam source device 10B at the time $t_0$, meets with the reference light beam having a frequency $f_1$, which has been radiated out of the laser beam source device 10B at the time $t_1$ (as illustrated in FIG. 8), and the wave fronts of the two light beams are matched with each other. Therefore, a beat signal of the interference light beam, which is caused to occur by the wavefront matching, is obtained such that the intensity of the beat signal may repeatedly become high and low at a frequency equal to the difference $(f_1-f_0)$ between the frequencies of the two light beams subjected to the wavefront matching.

Also, at the quarter-wave plate 12, the second backward scattered light beam (having the frequency $f_0$) of the laser beam, which has been radiated out of the laser beam source device 10B at the time $t_0$, meets with the reference light beam having a frequency $f_2$, which has been radiated out of the laser beam source device 10B at the time $t_2$ that is later than the time $t_1$ by a length of time of $2d/c$ (resulting from the division of the distance $2d$ two times as long as the thickness d of the cornea 210 by the light velocity c), and the wave fronts of the two light beams are matched with each other. Therefore, a beat signal of the interference light beam, which is caused to occur by the wavefront matching, is obtained such that the intensity of the beat signal may repeatedly become high and low at a frequency equal to the difference $(f_2-f_0)$ between the frequencies of the two light beams subjected to the wavefront matching.

From the laser beam source device 10B, the laser beam, the frequency of which changes with the passage of time, is successively radiated out. However, since the difference between the optical path length of the first backward scattered light beam and the optical path length of the second backward scattered light beam is invariable, the frequencies of the beat signals caused to occur by the interference with the respective backward scattered light beams are kept constant.

Each of the beat signal, which is caused to occur by the first backward scattered light beam, and the intensity or which repeatedly becomes high and low at the frequency equal to the difference $(f_1-f_0)$, and the beat signal, which is caused to occur by the second backward scattered light beam, and the intensity of which repeatedly becomes high and low at the frequency equal to the difference $(f_2-f_0)$, is guided from the polarization plane keeping coupler 61 into the third polarization plane keeping fiber 47 and detected by the photodetector 71.

The photodetector 71 calculates the intensity of each backward scattered light beam from the detected intensity of the beat signal and with the optical heterodyne detection processing. Also, the difference between the optical path lengths of the two backward scattered light beams, i.e. the thickness of the cornea 210, is calculated from the difference in frequency between the two beat signals and the inclination of the frequency sweeping in the laser beam source device 10B.

The signal processing circuit 81 calculates the refractive index $n_2$ of the aqueous humor with the formula shown above and in accordance with the thus calculated intensity $I_{R1}$ of the first backward scattered light beam, the intensity $I_{R2}$ of the second backward scattered light beam, the thickness d of the cornea 210, the already known refractive indexes $n_0$ and $n_1$, the reflectivity R1, and the absorbance a of the cornea 210. Also, the signal processing circuit 81 calculates the concentration G of glucose in the aqueous humor of the eyeball, which is subjected to the measurement, in accordance with the calculated refractive index $n_2$ of the aqueous humor and the correlation between the refractive index $n_2$ of the aqueous humor and the concentration G of glucose in the aqueous humor, which correlation has been stored in the signal processing circuit 81. The information representing the results of the calculation is fed from the signal processing circuit 81 into the display device 90.

The display device 90 displays the concentration G of glucose represented by the received information.

In this manner, with the glucose concentration measuring apparatus 101 of FIG. 7, the weak reflected light beams coming from the eyeball can be detected accurately with the optical heterodyne detection processing. Also, the concentration of glucose in the aqueous humor can be measured non-invasively and with the constitution simpler than with the conventional techniques.

With the conventional technique wherein the concentration of glucose is measured by measuring the absorbance of the aqueous humor, such that measurement error due to the presence of many kinds of constituents, which absorb the incident light beam, in the aqueous humor, it is necessary for the measurement to be repeated by using a plurality of kinds (ordinarily, at least five kinds) of light beams having different wavelengths. However, with this embodiment of the glucose concentration measuring apparatus 101 in accordance with the present invention, wherein the correspondence relationship between the refractive index with respect to one kind of light beam having a predetermined wavelength and the concentration of glucose is utilized, the measurement can be carried out by using only the light beam having the predetermined wavelength, and the time required to carry out the measurement can be kept markedly short.

In this embodiment of the glucose concentration measuring apparatus 101, as in the glucose concentration measuring apparatus 100' shown in FIG. 5, the ND filter 37 should preferably be located between the laser beam source device 10B and the half-wave plate 11, such that the ND filter 37 may be inclined by a predetermined angle with respect to the plane, which is normal to the direction of travel of the laser beam having been radiated out of the laser beam source device 10B. With the constitution provided with the ND filter 37, the return light beams, which return through the first polarization plane keeping fiber 45 toward the laser beam source device 10B, such as the interference light beams occurring from the interference of the first and second backward scattered light beams and the reference light beam with each other, can be prevented from impinging upon the laser beam source device 10B. As a result, the laser beam having a stable intensity can be irradiated to the eyeball 200, the intensity of each backward scattered light beam coming from the eyeball 200 can be kept stable, and the accuracy, with which each backward scattered light beam is measured, can be kept high. Further, the intensity of the laser beam impinging upon the eyeball 200 can be adjusted appropriately.

Figure 9:
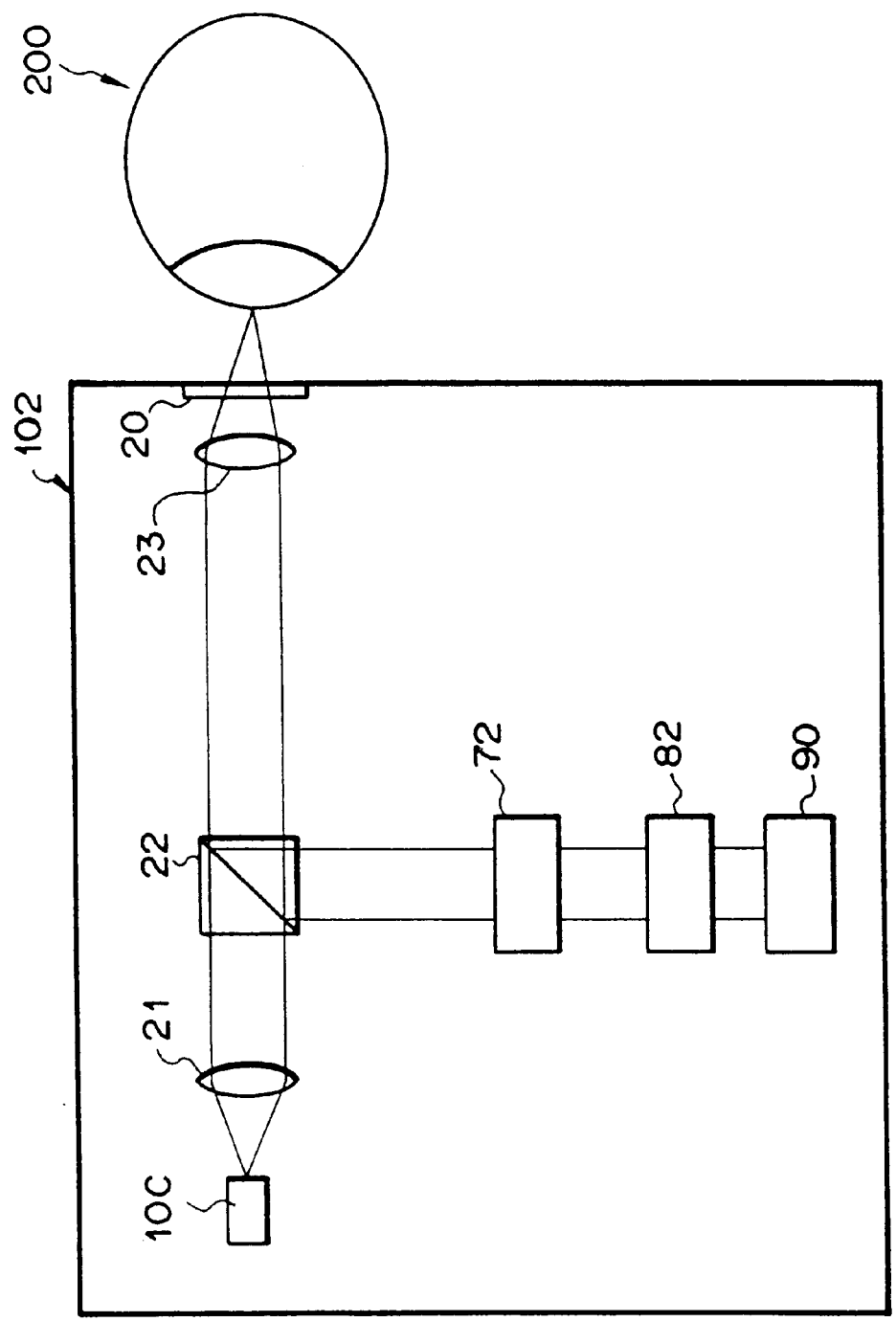
FIG. 9 is a schematic view showing an embodiment of the glucose concentration measuring apparatus for carrying out the fourth glucose concentration measuring method in accordance with the present invention.

FIG. 9 is a schematic view showing an embodiment of the glucose concentration measuring apparatus for carrying out the fourth glucose concentration measuring method in accordance with the present invention.

With reference to FIG. 9, a glucose concentration measuring apparatus 102 comprises a Ti:sapphire laser beam source device (hereinbelow referred to simply as the light source device) 10C for radiating out an ultrashort pulsed light beam. The glucose concentration measuring apparatus 102 also comprises a lens 21 for collimating the ultrashort pulsed light beam, which has been radiated out of the light source device 10C. The glucose concentration measuring apparatus 102 further comprises a converging lens 23 for converging the collimated ultrashort pulsed light beam onto the interfaces $R_1$ and $R_2$ in the eyeball 200, and the external light cut-off filter 20 for transmitting only the reflected light beams coming from the eyeball 200 (i.e., only the first backward scattered light beam, which is the reflected light beam coming from the interface $R_1$ between the cornea 210 and the ambient air 300, and the second backward scattered light beam, which is the reflected light beam coming from the interface $R_2$ between the cornea 210 and the anterior aqueous chamber 220). The glucose concentration measuring apparatus 102 still further comprises a beam splitter 22 for transmitting the light beam, which has been collimated by the lens 21, and reflecting the light beams, which have been reflected from the eyeball 200 and have passed through the external light cut-off filter 20. The glucose concentration measuring apparatus 102 also comprises a photodetector 72 for carrying out time series measurement of each of the intensity of the first backward scattered light beam and the intensity of the second backward scattered light beam of the ultrashort pulsed light beam. The photodetector 72 may be a streak camera, or the like. The glucose concentration measuring apparatus 102 further comprises a signal processing circuit 82 for calculating the refractive index $n_2$ of the aqueous humor, which fills the anterior aqueous chamber 220 of the eyeball 200, from the intensity of the light beam, which has been detected by the photodetector 72, and calculating the concentration G of glucose in the aqueous humor in accordance with the calculated refractive index $n_2$ of the aqueous humor and the correlation between the refractive index $n_2$ of the aqueous humor and the concentration G of glucose in the aqueous humor, which correlation has been stored in the signal processing circuit 82. The glucose concentration measuring apparatus 102 still further comprises the display device 90 for displaying the calculated concentration G of glucose in the aqueous humor.

The signal processing circuit 82 has the functions for the refractive index calculating means, the glucose concentration calculating means, and the storage section.

The ultrashort pulsed light beam is emitted for a very short time on the order of, for example, femtoseconds to picoseconds.

How the glucose concentration measuring apparatus 102 of FIG. 9 operates will be described hereinbelow.

Firstly, the ultrashort pulsed light beam is radiated out of the light source device 10C. The ultrashort pulsed light beam is collimated by the lens 21 and passes through the beam splitter 22. The ultrashort pulsed light beam is then converged by the converging lens 23 and is caused to impinge upon the eyeball 200.

The ultrashort pulsed light beam, which has impinged upon the eyeball 200, is reflected from the interface $R_1$ between the cornea 210 and the ambient air 300 and from the interface $R_2$ between the anterior aqueous chamber 220 and the cornea 210. Each of the first backward scattered light beam, which comes from the interface $R_1$, and the second backward scattered light beam, which comes from the interface $R_2$, passes through the external light cut-off filter 20, is reflected from the beam splitter 22, and impinges upon the photodetector 72 capable of effecting time resolution.

At this time, the timings, with which the first backward scattered light beam and the second backward scattered light beam emanate from the eyeball 200, are different from each other. Specifically, the first backward scattered light beam emanates firstly from the eyeball 200, and thereafter the second backward scattered light beam emanates from the eyeball 200. Also, each of the backward scattered light beams is the ultrashort pulsed light beam. The emission period of the ultrashort pulsed light beam is shorter than the difference in time for passage corresponding to the difference in depth between the interface $R_1$ and the interface $R_2$, from which the first and second backward scattered light beams come. Therefore, the backward scattered light beams emanate from the eyeball 200 one after the other such that they may be separated perfectly.

Figure 10:
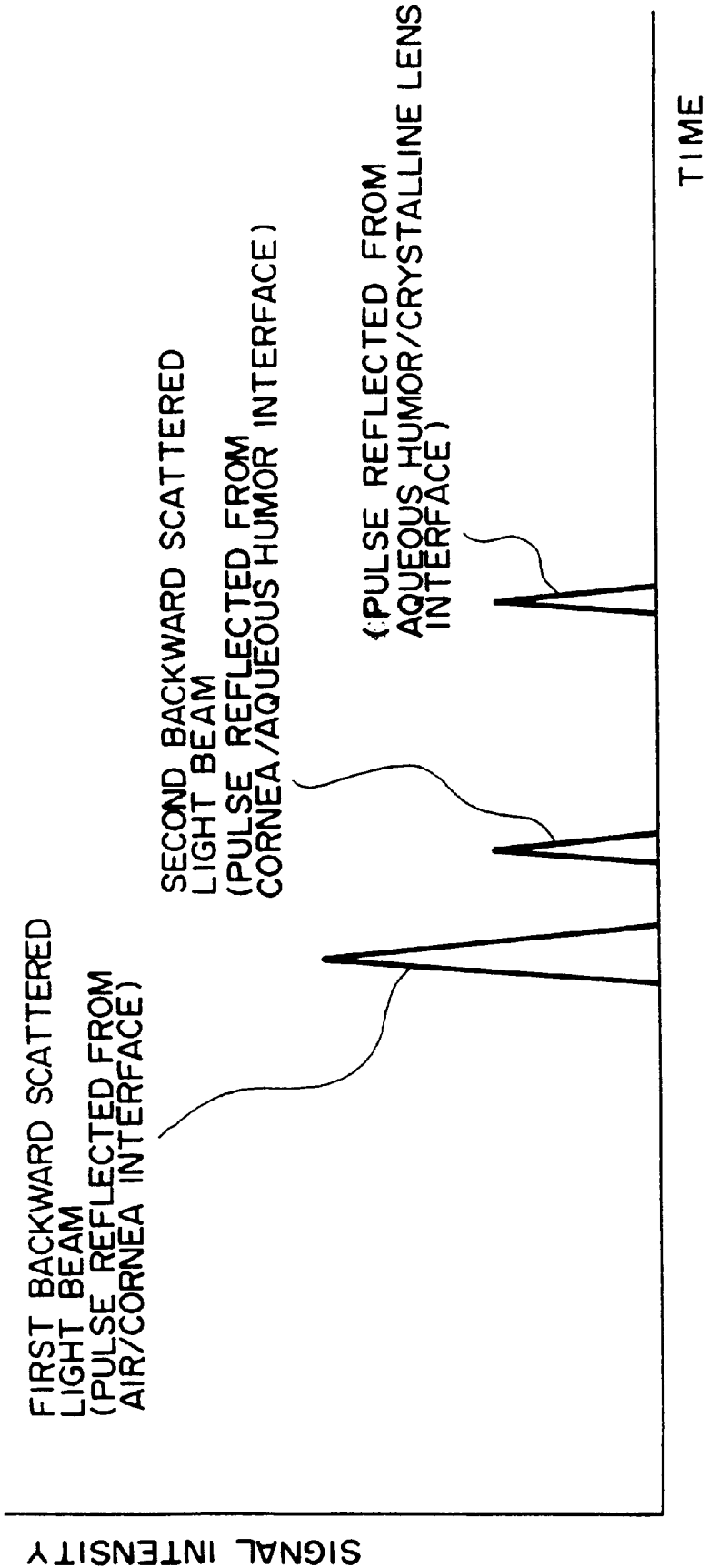
FIG. 10 is a graph showing intensities of light beams detected with a photodetector capable of effecting time resolution.

In this manner, the backward scattered light beams, which emanate successively from the eyeball 100, are successively detected by the photodetector 72 capable of effecting time resolution. FIG. 10 shows the intensities of the backward scattered light beams, which are time-resolved and detected by the photodetector 72 on the time series basis.

The amount of each backward scattered light beam can be calculated by integrating the intensity of each backward scattered light beam with respect to time. Also, the thickness of the cornea 210 can be calculated from the time, which has elapsed between when the first backward scattered light beam is detected and when the second backward scattered light beam is detected.

The signal processing circuit 82 calculates the refractive index $n_2$ of the aqueous humor with the formula shown above and in accordance with the thus calculated intensity $I_{R1}$ of the first backward scattered light beam, the intensity $I_{R2}$ of the second backward scattered light beam, the thickness d of the cornea 210, the already known refractive indexes $n_0$ and $n_1$, the reflectivity R1, and the absorbance a of the cornea 210. Also, the signal processing circuit 82 calculates the concentration G of glucose in the aqueous humor of the eyeball, which is subjected to the measurement, in accordance with the calculated refractive index $n_2$ of the aqueous humor and the correlation between the refractive index $n_2$ of the aqueous humor and the concentration G of glucose in the aqueous humor, which correlation has been stored in the signal processing circuit 82. The information representing the results of the calculation is fed from the signal processing circuit 82 into the display device 90.

The display device 90 displays the concentration G of glucose represented by the received information.

In this manner, with the glucose concentration measuring apparatus 102 of FIG. 9, the technique for the separate detection on the time axis with the ultrashort pulsed light beam is employed, in which the difference in optical path length between the first backward scattered light beam and the second backward scattered light beam is utilized, the difference occurring due to the difference between the positions of occurrence of the first and second backward scattered light beams. Therefore, it is possible to accurately detect each of the intensity $I_{R1}$ of the weak first backward scattered light beam of the incident light beam, the first backward scattered light beam coming from the interface between the cornea of the eyeball and the ambient air, and the intensity $I_{R2}$ of the weak second backward scattered light beam of the incident light beam, the second backward scattered light beam coming from the interface between the cornea and the anterior aqueous chamber of the eyeball. Also, the refractive index of the aqueous humor (the refractive index of the aqueous humor in the vicinity of the interface with the cornea) can be calculated from the intensity of the first backward scattered light beam and the intensity of the second backward scattered light beam. The concentration of glucose in the aqueous humor can then be determined non-invasively and with a high accuracy in accordance with the correspondence relationship between the refractive index of the aqueous humor and the concentration of glucose in the aqueous humor, which relationship has been found previously, and in accordance with the calculated refractive index of the aqueous humor. Also, the concentration of glucose in the aqueous humor can be measured non-iniasively and with the constitution simpler than with the conventional techniques.

With the conventional technique wherein the concentration of glucose is measured by measuring the absorbance of the aqueous humor, such that measurement error due to the presence of many kinds of constituents, which absorb the incident light beam, in the aqueous humor, it is necessary for the measurement to be repeated by using a plurality of kinds (ordinarily, at least five kinds) of light beams having different wavelengths. However, with this embodiment of the glucose concentration measuring apparatus 102 in accordance with the present invention, wherein the correspondence relationship between the refractive index with respect to one kind of light beam having a predetermined wavelength and the concentration of glucose is utilized, the measurement can be carried out by using only the light beam having the predetermined wavelength, and the time required to carry out the measurement can be kept markedly short.

Figure 11:
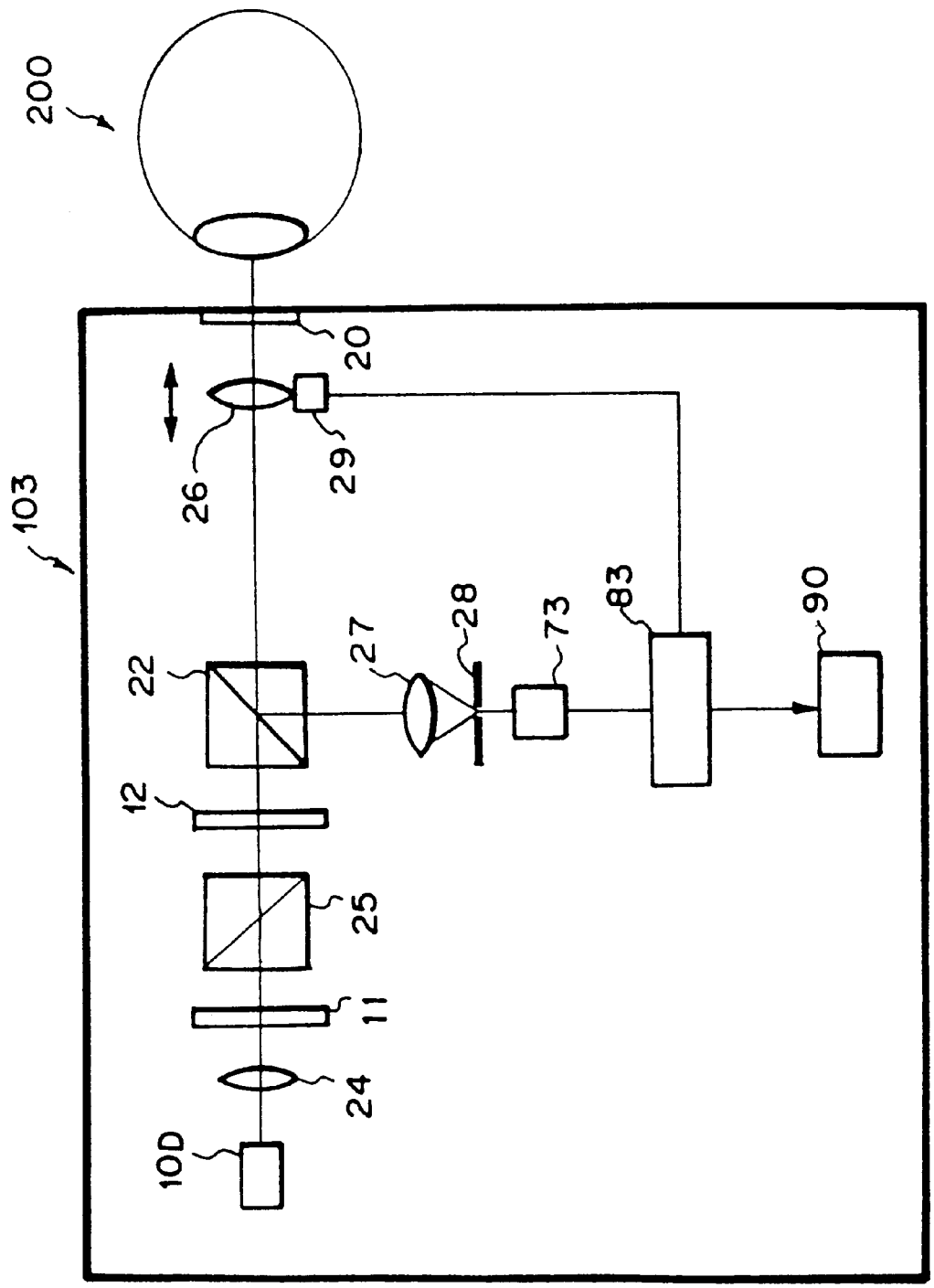
FIG. 11 is a schematic view showing an embodiment of the glucose concentration measuring apparatus for carrying out the fifth glucose concentration measuring method in accordance with the present invention.

FIG. 11 is a schematic view showing an embodiment of the glucose concentration measuring apparatus for carrying out the fifth glucose concentration measuring method in accordance with the present invention.

With reference to FIG. 11, a glucose concentration measuring apparatus 103 comprises a laser beam source device 10D for producing a laser beam, and a lens 24 for collimating the laser beam having been radiated out of the laser beam source device 10D. The glucose concentration measuring apparatus 103 also comprises the half-wave plate 11 for converting the laser beam, which has been collimated by the lens 24, into a linearly polarized light beam, and a polarization beam splitter 25 for transmitting the linearly polarized light beam. The glucose concentration measuring apparatus 103 further comprises the quarter-wave plate 12 for converting the light beam, which has passed through the polarization beam splitter 25, into a circularly polarized light beam, and the beam splitter 22 for transmitting a portion of the circularly polarized light beam. The glucose concentration measuring apparatus 103 still further comprises a converging lens 26 capable of moving along the optical axis direction such that it may converge the circularly polarized light beam onto the interface $R_1$ between the cornea 210 of the eyeball 200, which lies at a predetermined position, and the ambient air 300 and onto the interface $R_2$ between the cornea 210 and the anterior aqueous chamber 220. The glucose concentration measuring apparatus 103 also comprises a lens moving device 29 for moving the converging lens 26 along the optical axis direction. The glucose concentration measuring apparatus 103 further comprises the external light cut-off filter 20 for transmitting only the reflected light beams coming from the eyeball 200 (i.e., only the first backward scattered light beam, which is the reflected light beam coming from the interface $R_1$ between the cornea 210 and the ambient air 300, and the second backward scattered light beam, which is the reflected light beam coming from the interface $R_2$ between the cornea 210 and the anterior aqueous chamber 220). The glucose concentration measuring apparatus 103 still further comprises a converging lens 27 which constitutes the confocal optical system together with the converging lens 26. The glucose concentration measuring apparatus 103 also comprises a pinhole plate 28 having a pinhole allowing the light beam, which is converged at a focusing point opposite to the eyeball side focusing point of the confocal optical system, to pass therethrough. The glucose concentration measuring apparatus 103 further comprises a photodetector 73 for detecting the light beam, which has passed through the pinhole of the pinhole plate 28. The glucose concentration measuring apparatus 103 still further comprises a signal processing circuit 83 for calculating the refractive index $n_2$ of the aqueous humor, which fills the anterior aqueous chamber 220 of the eyeball 200, from the intensity values $I_{R1}$ and $I_{R2}$ of the reflected light beams (i.e., the first backward scattered light beam and the second backward scattered light beam), which come from the interfaces $R_1$ and $R_2$ in the eyeball 200 and have been detected by the photodetector 73, and the thickness d of the cornea 210, which is calculated from the distance of movement of the converging lens 26 moved by the lens moving device 29. The signal processing circuit 83 also calculates the concentration G of glucose in the aqueous humor in accordance with the calculated refractive index $n_2$ of the aqueous humor and the correlation between the refractive index $n_2$ of the aqueous humor and the concentration G of glucose in the aqueous humor, which correlation has been stored in the signal processing circuit 83. The glucose concentration measuring apparatus 103 also comprises the display device 90 for displaying the calculated concentration G of glucose in the aqueous humor.

The signal processing circuit 83 has the functions for the refractive index calculating means, the glucose concentration calculating means, and the storage section.

How the glucose concentration measuring apparatus 103 of FIG. 11 operates will be described hereinbelow.

Firstly, the laser beam is radiated out of the laser beam source device 10D. The laser beam is collimated by the lens 24 and successively passes through the half-wave plate 11, the polarization beam splitter 25, and the quarter-wave plate 12. The half-wave plate 11, the polarization beam splitter 25, and the quarter-wave plate 12 constitute the return light cut-off optical system and prevent the reflected light beams, which come from the eyeball 200, from returning to and impinging upon the laser beam source device 10D.

The light beam (the laser beam), which has passed through the quarter-wave plate 12, passes through the beam splitter 22 and is irradiated to the eyeball 200 by the converging lens 26. At this time, the converging lens 26 is moved along the optical axis direction by the lens moving device 29, and the light beam irradiated to the eyeball 200 is thereby firstly converged onto the interface $R_1$. Information representing the position, to which the converging lens 26 has been moved by the lens moving device 29, is fed into the signal processing circuit 83.

The light beam, which has been converged onto the interface $R_1$, is reflected as the first backward scattered light beam by the interface $R_1$. The first backward scattered light beam passes through the external light cut-off filter 20 and is converged to the pinhole of the pinhole plate 28 by the effects of the converging lens 26, the beam splitter 22, and the converging lens 27, which constitute the confocal optical system. The first backward scattered light beam passes through the pinhole of the pinhole plate 28 and is detected by the photodetector 73. The light beam detected at this time is only the first backward scattered light beam. The other light beams, which have been reflected from the other interfaces in the eyeball 200, are cutoff by the pinhole plate 28 and are not detected by the photodetector 73. Therefore, at this time, only the intensity of the first backward scattered light beam can be detected.

Thereafter, the converging lens 26 is moved along the optical axis direction by the lens moving device 29, and the light beam, which has been irradiated to the eyeball 200, is thereby converged onto the interface $R_2$. Information representing the position, to which the converging lens 26 has been moved by the lens moving device 29, is fed into the signal processing circuit 83. The signal processing circuit 83 calculates the distance of movement of the converging lens 26 in accordance with the information representing the position, to which the converging lens 26 has been moved for converging the light beam onto the interface $R_1$, and the information representing the position, to which the converging lens 26 has been moved for converging the light beam onto the interface $R_2$. The signal processing circuit 83 also calculates the distance between the interface $R_1$ and the interface $R_2$, i.e. the thickness d of the cornea 210, in accordance with the focal length of the converging lens 26 and the focal length of the converging lens 27.

The light beam, which has been converged onto the interface $R_2$, is reflected as the second backward scattered light beam by the interface $R_2$. The second backward scattered light beam passes through the external light cut-off filter and is converged to the pinhole of the pinhole plate 28 by the effects of the converging lens 26, the beam splitter 22, and the converging lens 27, which constitute the confocal optical system. The second backward scattered light beam passes through the pinhole of the pinhole plate 28 and is detected by the photodetector 73. The light beam detected at this time is only the second backward scattered light beam. The other light beams, which have been reflected from the other interfaces in the eyeball 200, are cut off by the pinhole plate 28 and are not detected by the photodetector 73. Therefore, at this time, only the intensity of the second backward scattered light beam can be detected.

The signal processing circuit 83 calculates the refractive index $n_2$ of the aqueous humor with the formula shown above and in accordance with the thus calculated intensity $I_{R1}$ of the first backward scattered light beam, the intensity $I_{R2}$ of the second backward scattered light beam, the thickness d of the cornea 210, the already known refractive indexes $n_0$ and $n_1$, the reflectivity R1, and the absorbance a of the cornea 210. Also, the signal processing circuit 83 calculates the concentration G of glucose in the aqueous humor of the eyeball, which is subjected to the measurement, in accordance with the calculated refractive index $n_2$ of the aqueous humor and the correlation between the refractive index $n_2$ of the aqueous humor and the concentration G of glucose in the aqueous humor, which correlation has been stored in the signal processing circuit 83. The information representing the results of the calculation is fed from the signal processing circuit 83 into the display device 90.

The display device 90 displays the concentration G of glucose represented by the received information.

In this manner, with the glucose concentration measuring apparatus 103 of FIG. 11, the technique for the separate detection in the spatial domain with the confocal optical system is employed, in which the difference in optical path length between the first backward scattered light beam and the second backward scattered light beam is utilized, the difference occurring due to the difference between the positions of occurrence of the first and second backward scattered light beams. Therefore, it is possible to accurately detect each of the intensity $I_{R1}$ of the weak first backward scattered light beam of the incident light beam, the first backward scattered light beam coming from the interface between the cornea of the eyeball and the ambient air, and the intensity $I_{R2}$ of the weak second backward scattered light beam of the incident light beam, the second backward scattered light beam coming from the interface between the cornea and the anterior aqueous chamber of the eyeball. Also, the refractive index of the aqueous humor (the refractive index of the aqueous humor in the vicinity of the interface with the cornea) can be calculated from the intensity of the first backward scattered light beam and the intensity of the second backward scattered light beam. The concentration of glucose in the aqueous humor can then be determined non-invasively and with a high accuracy in accordance with the correspondence relationship between the refractive index of the aqueous humor and the concentration of glucose in the aqueous humor, which relationship has been found previously, and in accordance with the calculated refractive index of the aqueous humor. Also, the concentration of glucose in the aqueous humor can be measured non-invasively and with the constitution simpler than with the conventional techniques.

With the conventional technique wherein the concentration of glucose is measured by measuring the absorbance of the aqueous humor, such that measurement error due to the presence of many kinds of constituents, which absorb the incident light beam, in the aqueous humor, it is necessary for the measurement to be repeated by using a plurality of kinds (ordinarily, at least five kinds) of light beams having different wavelengths. However, with this embodiment of the glucose concentration measuring apparatus 103 in accordance with the present invention, wherein the correspondence relationship between the refractive index with respect to one kind of light beam having a predetermined wavelength and the concentration of glucose is utilized, the measurement can be carried out by using only the light beam having the predetermined wavelength, and the time required to carry out the measurement can be kept markedly short.

Figure 12:
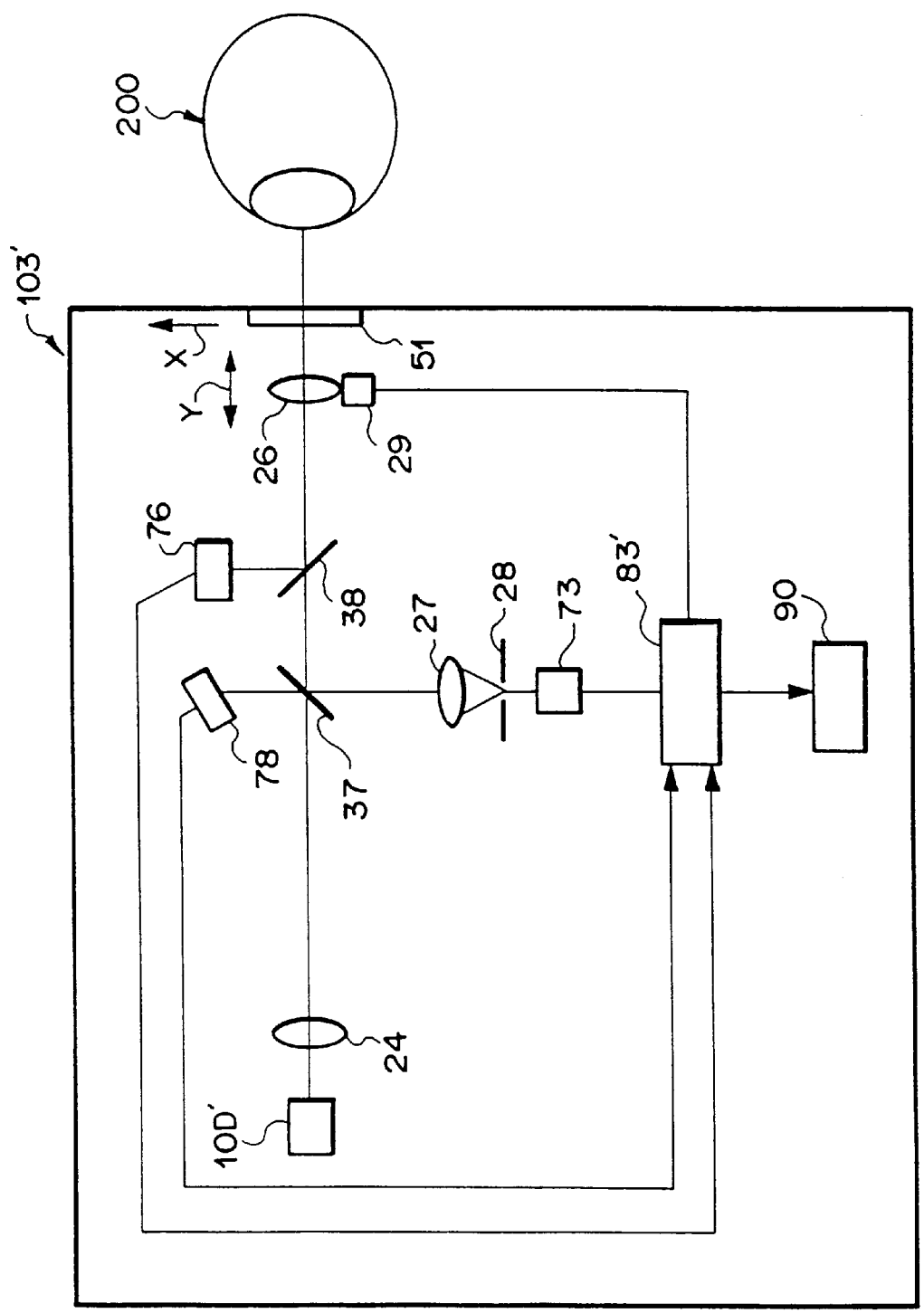
FIG. 12 is a schematic view showing a different embodiment of the glucose concentration measuring apparatus for carrying out the fifth glucose concentration measuring method in accordance with the present invention.

FIG. 12 is a schematic view showing a different embodiment of the glucose concentration measuring apparatus for carrying out the fifth glucose concentration measuring method in accordance with the present invention.

With reference to FIG. 12, a glucose concentration measuring apparatus 103' comprises a semiconductor laser beam source device 10D' for radiating out a laser beam, which has wavelengths falling in the visible region (<1,400 nm), with an output power of 3 mW to 4 mW. The glucose concentration measuring apparatus 103' also comprises the lens 24 for collimating the laser beam, which has been radiated out of the semiconductor laser beam source device 10D'. The glucose concentration measuring apparatus 103' further comprises the ND filter 37, which is inclined by an angle of approximately 45 degrees with respect to the plane that is normal to the direction of travel of the laser beam heaving been collimated by the lens 24. The ND filter 37 has an OD value of 3 to 4. Of the laser beam having been having been collimated by the lens 24, the ND filter 37 transmits only the portion of approximately several microwatts and reflects the remaining major portion of the laser beam toward a radiated light intensity detector 78 that is located at a position along the direction, which intersects approximately perpendicularly to the direction of travel of the laser beam. The glucose concentration measuring apparatus 103' still further comprises the converging lens 26 capable of moving along the optical axis direction (the directions indicated by the double headed arrow Y) such that it may converge the laser beam, which has passed through the ND filter 37, onto a reflection surface of a standard reflecting plate 51, which will be described later, onto the interface $R_1$ between the cornea 210 of the eyeball 200, which lies at a predetermined position, and the ambient air 300, and onto the interface $R_2$ between the cornea 210 and the anterior aqueous chamber 220. The glucose concentration measuring apparatus 103' also comprises the lens moving device 29 for moving the converging lens 26 along the optical axis direction. The glucose concentration measuring apparatus 103' further comprises the standard reflecting plate 51, which has the reflection surface that is normal to the optical axis of the converging lens 26. The standard reflecting plate 51 is capable of moving between a retreated position that allows the laser beam, which has been converged by the converging lens 26, to be converged onto the eyeball 200 lying at the predetermined position, and a reflecting position that reflects the laser beam, which has been converged by the converging lens 26, reversely to the direction of travel of the converged laser beam. The glucose concentration measuring apparatus 103' still further comprises the converging lens 27, which constitutes the confocal optical system together with the converging lens 26 with respect to the reflected light beams (laser beams) coming from the eyeball 200 (i.e., the first backward scattered light beam, which is the reflected light beam coming from the interface $R_1$ between the cornea 210 and the ambient air 300, and the second backward scattered light beam, which is the reflected light beam coming from the interface $R_2$ between the cornea 210 and the anterior aqueous chamber 220) and the reflected light beam (laser beam) coming from the standard reflecting plate 51. The glucose concentration measuring apparatus 103' also comprises the pinhole plate 28 having a pinhole allowing the light beam, which is converged at a focusing point opposite to the focusing point on the eyeball side or on the standard reflecting plate side of the confocal optical system, to pass therethrough. The glucose concentration measuring apparatus 103' further comprises the photodetector 73 for detecting the light beam, which has passed through the pinhole of the pinhole plate 28. The glucose concentration measuring apparatus 103' still further comprises an infrared reflecting mirror 38 for reflecting infrared rays, which are radiated from the surface of the cornea 210, and an infrared temperature sensor 76 for detecting the infrared rays, which have been reflected from the infrared reflecting mirror 38, and thereby measuring the surface temperature of the cornea 210. The glucose concentration measuring apparatus 103' also comprises a signal, processing circuit 83'. The signal processing circuit 83' calculates the reflectivity R1 of the interface $R_1$ between the cornea 210 of the eyeball 200 and the ambient air 300 and the reflectivity R2 of the interface $R_2$ between the cornea 210 and the anterior aqueous chamber 220 in accordance with the intensity Is of the reflected light beam, which comes from the standard reflecting plate 51 and has been detected by the photodetector 73, the intensity values $I_{R1}$ and $I_{R2}$ of the reflected light beams (i.e., the first backward scattered light beam and the second backward scattered light beam), which come from the interfaces $R_1$ and $R_2$ in the eyeball 200 and have been detected by the photodetector 73, and the set reflectivity Rs of the standard reflecting plate 51. Also, the signal processing circuit 83' calculates the refractive index $n_1$ of the cornea 210 from the calculated reflectivity R1 and the refractive index $n_0$ of the ambient air 300 and thereafter calculates the refractive index $n_2$ of the aqueous humor, which fills the anterior aqueous chamber 220 of the eyeball 200, from the calculated refractive index $n_1$ of the cornea 210 and the reflectivity R2. Further, the signal processing circuit 83' corrects the calculated refractive index $n_2$ of the aqueous humor in accordance with temperature by making reference to an intra-eyeball temperature distribution table (shown in FIG. 13). The signal processing circuit 83' then calculates the concentration G of glucose in the aqueous humor in accordance with a corrected refractive index $n_2'$ of the aqueous humor and the correlation between the refractive index $n_2'$ of the aqueous humor and the concentration G of glucose in the aqueous humor, which correlation has been stored in the signal processing circuit 83'. The glucose concentration measuring apparatus 103' further comprises the display device 90 for displaying the calculated concentration G of glucose in the aqueous humor.

The signal processing circuit 83' has the functions for the refractive index calculating means, the glucose concentration calculating means, and the storage section.

Figure 13:
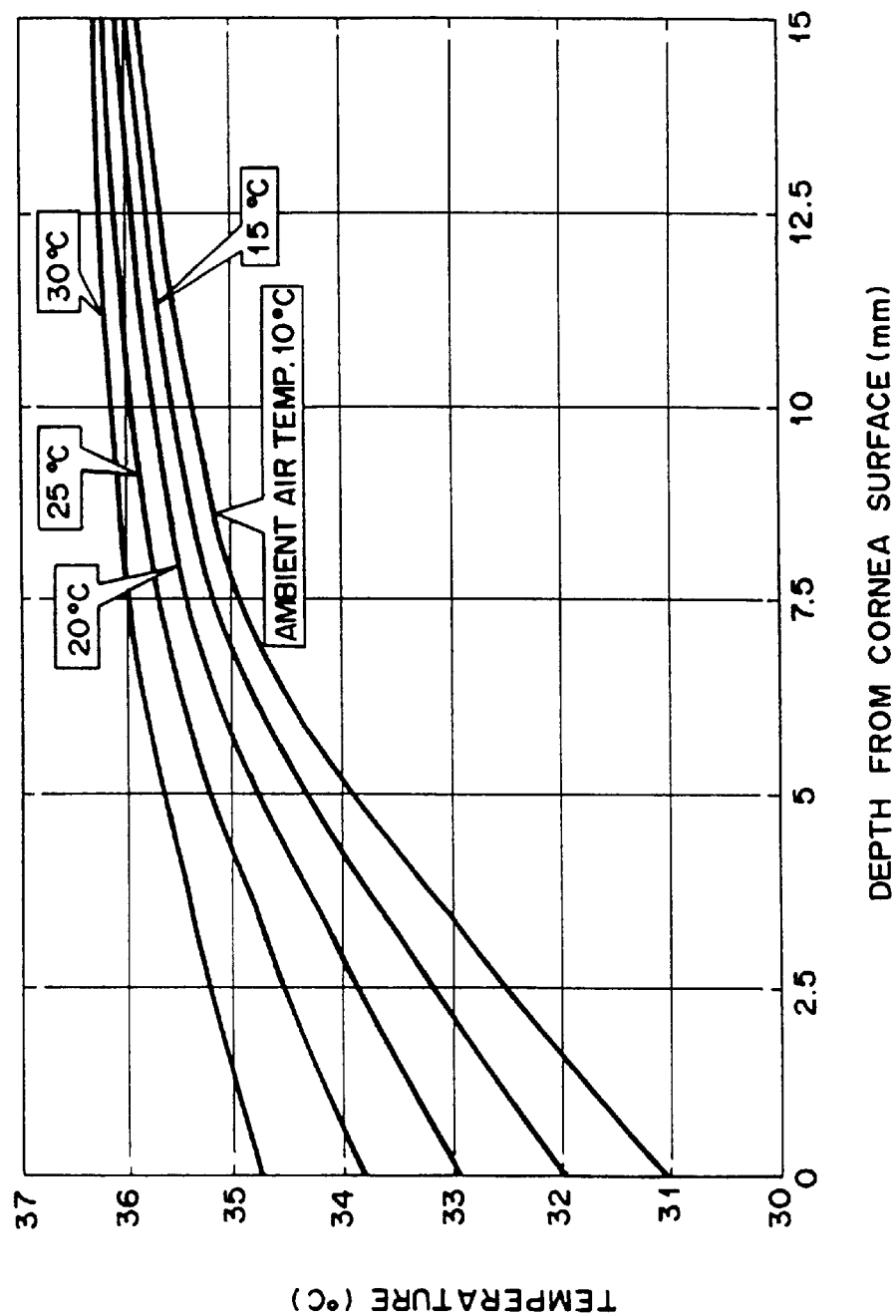
FIG. 13 is a graph showing intra-eyeball temperature distributions, which are obtained when a deep portion temperature is 36.5° C. and ambient air temperatures are 10° C., 15° C., 20° C., 25° C., and 30° C.

As illustrated in FIG. 13, the intra-eyeball temperature distribution table, which is stored in the signal processing circuit 83', represents the distributions in accordance with the cornea surface temperatures, which distributions are obtained when a deep portion temperature is 36.5° C. The intra-eyeball temperature distribution table is set previously through experiments or clinical study. The intra-eyeball temperature distribution may be set as the look-up table, a function, or the like. Also, as illustrated in FIG. 13, in cases where the intra-eyeball temperature distribution is set discretely in accordance with a plurality of values of the surface temperature of the cornea, the temperature distribution conforming to the measured surface temperature of the cornea may be determined by carrying out interpolating operations, or the like.

How this embodiment of the glucose concentration measuring apparatus 103' operates will be described hereinbelow.

Firstly, the standard reflecting plate 51 is moved to the reflecting position (i.e., the position illustrated in FIG. 12). Thereafter, the semiconductor laser beam source device 10D' radiates out the laser beam, which has wavelengths falling in the visible region, with an output power of 3 mW to 4 mW. The laser beam is collimated by the lens 24 and impinges upon the ND filter 37. of the incident laser beam, the ND filter 37 transmits only the portion of approximately several microwatts and reflects the remaining major portion of the laser beam toward the radiated light intensity detector 78.

The radiated light intensity detector 78 detects the intensity $I_0$ of the incident laser beam and feeds the information, which represents the detected intensity, into the signal processing circuit 83'.

The laser beam, which has passed through the ND filter 37, passes through the infrared reflecting mirror 38 and is irradiated to the standard reflecting plate 51 by the converging lens 26. At this time, the converging lens 26 is moved along the optical axis direction by the lens moving device 29, and the laser beam is converged onto the standard reflecting plate 51. The laser beam, which has been converged onto the standard reflecting plate 51, is reflected with the predetermined reflectivity Rs. The reflected laser beam is converged to the pinhole of the pinhole plate 28 by the effects of the converging lens 26, the ND filter 37, and the converging lens 27, which constitute the confocal optical system. The laser beam passes through the pinhole of the pinhole plate 28 and is detected by the photodetector 73. Approximately all of the reflected laser beam is reflected by the ND filter 37 toward the converging lens 27, and little reflected laser beam passes through the ND filter 37 toward the semiconductor laser beam source device 10D'. Therefore, the output power of the semiconductor laser beam source device 10D' can be prevented from becoming unstable due to impingement of the reflected laser beam. As a result, the laser beam having stable intensity can be radiated out of the semiconductor laser beam source device 10D'.

The intensity of the reflected laser beam, which has be(en detected by the photodetector 73, may be represented by Is. The factor, which represents optical loss in the forward and backward optical paths between the ND filter 37 and the standard reflecting plate 51 and in the optical path from the ND filter 37 to the photodetector 73, may be represented by k. The known reflectivity of the standard reflecting plate 51 may be represented by Rs, and the intensity of the laser beam detected by the radiated light intensity detector 78 may be represented by $I_0$. In such cases, the intensity Is of the reflected laser beam may be represented by Formula (9) shown below.

$$Is = I_0 \times k \times Rs \tag{9}$$

Thereafter, the standard reflecting plate 51 is moved in the direction indicated by the arrow X in FIG. 12 and is set at the retreated position. As a result, the laser beam, which has been converged by the converging lens 26, is irradiated to the eyeball 200. At this time, the converging lens 26 is moved along the optical axis direction by the lens moving device 29, and the laser beam irradiated to the eyeball 200 is thereby firstly converged onto the interface $R_1$.

The laser beam, which has been converged onto the interface $R_1$, is reflected as the first backward scattered light beam by the interface $R_1$. The first backward scattered light beam is converged to the pinhole of the pinhole plate 28 by the effects of the converging lens 26, the ND filter 37, and the converging lens 27, which constitute the confocal optical system. The first backward scattered light beam passes through the pinhole of the pinhole plate 28 and is detected by the photodetector 73. The light beam detected at this time is only the first backward scattered light beam. The other light beams, which have been reflected from the other interfaces in the eyeball 200, are cut off by the pinhole plate 28 and are not detected by the photodetector 73. Therefore, at this time, only the intensity $I_{R1}$ of the first backward scattered light beam can be detected.

Thereafter, the converging lens 26 is moved along the optical axis direction by the lens moving device 29, and the laser beam, which has been irradiated to the eyeball 200, is thereby converged onto the interface $R_2$.

The laser beam, which has been converged onto the interface $R_2$. is reflected as the second backward scattered light beam by the interface $R_2$. The second backward scattered light beam is converged to the pinhole of the pinhole plate 28 by the effects of the converging lens 26, the ND filter 37, and the converging lens 27, which constitute the confocal optical system. The second backward scattered light beam passes through the pinhole of the pinhole plate 28 and is detected by the photodetector 73. The light beam detected at this time is only the second backward scattered light beam. The other light beams, which have been reflected from the other interfaces in the eyeball 200, are cut off by the pinhole plate 28 and are not detected by the photodetector 73. Therefore, at this time, only the intensity $I_{R2}$ of the second backward scattered light beam can be detected.

Also, infrared rays radiated from the surface of the cornea 210 of the eyeball 200 impinges upon the infrared temperature sensor 76 via the converging lens 26 and the infrared reflecting mirror 38, and the temperature of the surfaces of the cornea 210 is thereby measured. Information, which represents the measured temperature of the surface of the cornea 210, is fed into the signal processing circuit 83'.

The reflectivity of the interface $R_1$ in the eyeball 200 may be represented by R1, and the reflectivity of the interface $R_2$ may be represented by R2. In such cases, as in Formula (9) shown above, the intensity $I_{R1}$ and the intensity $I_{R2}$ of the backward scattered light beams may be represented by Formulas (7) and (8) shown below.

$$I_{R1} = I_0 \times k \times R1 \tag{7}$$

$$I_{R2} = I_0 \times k \times R2 \tag{8}$$

Formulas (5) and (6) shown below are derived from Formulas (7), (8), and (9) shown above. The signal processing circuit 83' calculates the reflectivity R1 and the reflectivity R2 of the interfaces from the known values of $I_{R1}$, $I_{R2}$, Is, and Rs.

$$R1 = Rs \times I_{R1}/Is \tag{5}$$

$$R2 = Rs \times I_{R2}/Is \tag{6}$$

The reflectivity R1 and the reflectivity R2 may be represented by Formulas (10) and (11) shown below by using the refractive index $n_0$ of the ambient air 300, the refractive index $n_1$ of the cornea 210, and the refractive index $n_2$ of the aqueous humor, which fills the anterior aqueous chamber 220.

$$R1=\{(n_0-n_1)/(n_0+n_1)\}^2 \qquad (10)$$

$$R2=\{(n_1-n_2)/(n_1+n_2)\}^2 \qquad (11)$$

Therefore, the signal processing circuit 83' calculates the refractive index $n_1$ of the cornea 210 with Formula (10) in accordance with the calculated reflectivity R1 and the refractive index $n_0$ of the ambient air 300. Also, the signal processing circuit 83' calculates the refractive index $n_2$ of the aqueous humor, which fills the anterior aqueous chamber 220, with Formula (11) in accordance with the calculated refractive index $n_1$ of the cornea 210 and the reflectivity R2.

Thereafter, the signal processing circuit 83' makes reference to the received surface temperature of the cornea 210 and the intra-eyeball temperature distribution table shown in FIG. 13 and calculates the intra-eyeball temperature distribution corresponding to the surface temperature of the cornea 210. In accordance with the calculated intra-eyeball temperature distribution, the signal processing circuit 83' calculates the temperature of the aqueous humor, which fills the anterior aqueous chamber 220. The depth position of the interface $R_2$ between the cornea 210 and the anterior aqueous chamber 220 containing the aqueous humor, which depth position is taken from the surface of the cornea 210, can be calculated from the distance of movement of the converging lens 26 moved by the lens moving device 29.

The correlation between the refractive index $n_2$ of the aqueous humor and the concentration G of glucose in the aqueous humor, which correlation has been stored in the signal processing circuit 83', is the one obtained when the temperature of the aqueous humor is equal to a predetermined value. Therefore, the calculated refractive index $n_2$ of the aqueous humor is corrected in accordance with the calculated temperature of the aqueous humor. The concentration G of glucose in the aqueous humor is calculated in accordance with the corrected refractive index $n_2'$ and the correlation described above. Information, which represents the results of the calculation, is fed into the display device 90.

The display device 90 displays the concentration G of glucose represented by the received information.

In this manner, with the glucose concentration measuring apparatus 103' of FIG. 12, the technique for the separate detection in the spatial domain with the confocal optical system is employed, in which the difference in optical path length between the first backward scattered light beam and the second backward scattered light beam is utilized, the difference occurring due to the difference between the positions of occurrence of the first and second backward scattered light beams. Therefore, it is possible to accurately detect each of the intensity $I_{R1}$ of the weak first backward scattered light beam of the incident light beam, the first backward scattered light beam coming from the interface between the cornea of the eyeball and the ambient air, and the intensity $I_{R2}$ of the weak second backward scattered light beam of the incident light beam, the second backward scattered light beam coming from the interface between the cornea and the anterior aqueous chamber of the eyeball. Also, the reflectivity values are calculated by taking the optical loss (the factor k) in the optical path into consideration as in Formulas (7), (8), and (9) shown above, and the refractive indexes of the cornea and the aqueous humor can be calculated with Formulas (10) and (11) shown above from the reflectivity values, which have been calculated by taking the optical loss into consideration. Therefore, the refractive index of the aqueous humor can be calculated more accurately. Further, during the period other than the measurements of the intensity values of the backward scattered light beams, the standard reflecting plate 51, which is employed in this embodiment, can be utilized as a barrier for preventing dust, or the like, from entering into the apparatus. Therefore, the standard reflecting plate 51 is also useful as the dust preventing means.

Furthermore, in cases where the refractive index of the aqueous humor is corrected in accordance with the temperature of the aqueous humor, even if the refractive index of water, which constitutes approximately 95% (by weight) of the weight of the constituents of the aqueous humor, fluctuates depending upon the temperature, the refractive index of the aqueous humor can be corrected in accordance with the fluctuation in the refractive index of water. Therefore, the concentration of glucose corresponding to the refractive index can be determined more accurately.

Also, with the glucose concentration measuring apparatus 103' of FIG. 12, wherein the ND filter 37 is employed, return light can be prevented from impinging upon the semiconductor laser beam source device 10D'. As other means for preventing the return light from impinging upon the semiconductor laser beam source device 10D', it may be considered to use a combination of a half-wave plate, a polarization beam splitter, and a quarter-wave plate. However, in such cases, since the polarization is utilized, the problems occur in that adverse effects of birefringence occurs at the cornea having the birefringence characteristics, and the refractive index cannot be obtained accurately. In cases where the ND filter is employed as in this embodiment, since it is not necessary to utilize polarization, such problems do not occur. Further, since the ND filter can reduce the intensity of the light beam impinging upon the eyeball 200, it is not necessary to provide a particular means for adjusting the MPE value.

The technique for calculating the refractive index of the aqueous humor by utilizing the standard reflecting plate, the technique for correcting the refractive index in accordance with the temperature, and the technique for preventing return light from impinging upon the light source devices by utilizing the ND filter, which techniques are employed in this embodiment, are also applicable to the aforesaid embodiments of the glucose concentration measuring apparatus in accordance with the present invention.

Figure 14:
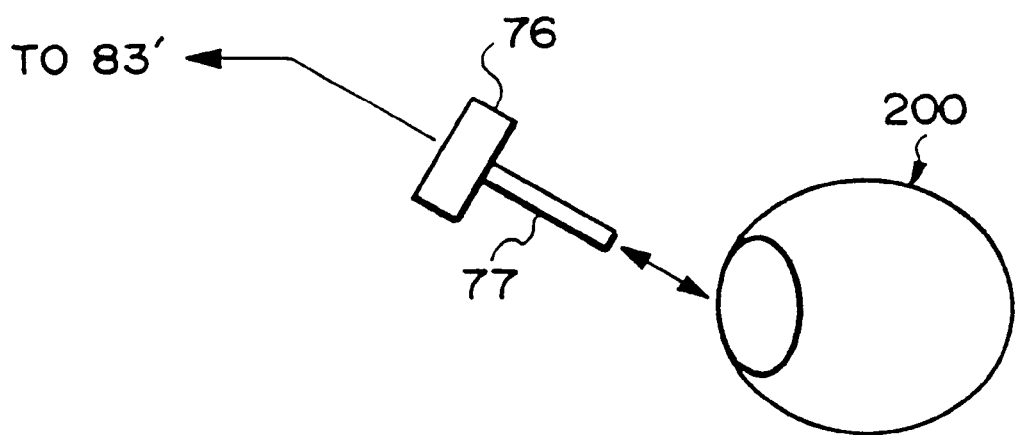
FIG. 14 is a schematic view showing a different example of an infrared temperature sensor (an infrared measuring means) for measuring a cornea surface temperature.

Besides the technique shown in FIG. 12, as illustrated in FIG. 14, the measurement of the surface temperature of the cornea 210 may be carried out by using a cylindrical member 77, which is located in the vicinity of the cornea 210 and connected to the sensing surface of the infrared temperature sensor 76. With the cylindrical member 77, infrared rays radiated from the cornea 210 can be detected with enhanced directivity by the infrared temperature sensor 76.

In lieu of the surface temperature of the cornea 210 being measured, the skin temperature in the vicinity of the cornea or the ambient air temperature in the vicinity of the cornea, which temperature has strong correlation with the surface temperature of the cornea, may be measured.

Also, both of the surface temperature of the cornea and the deep portion temperature in the eyeball may be measured, and the intra-eyeball temperature distribution may be calculated in accordance with them. In such cases, as the deep portion temperature in the eyeball, the temperature at a deep portion in the external auditory miatus may be measured by measuring infrared rays radiated from the deep portion in the external auditory miatus.

Figure 15:
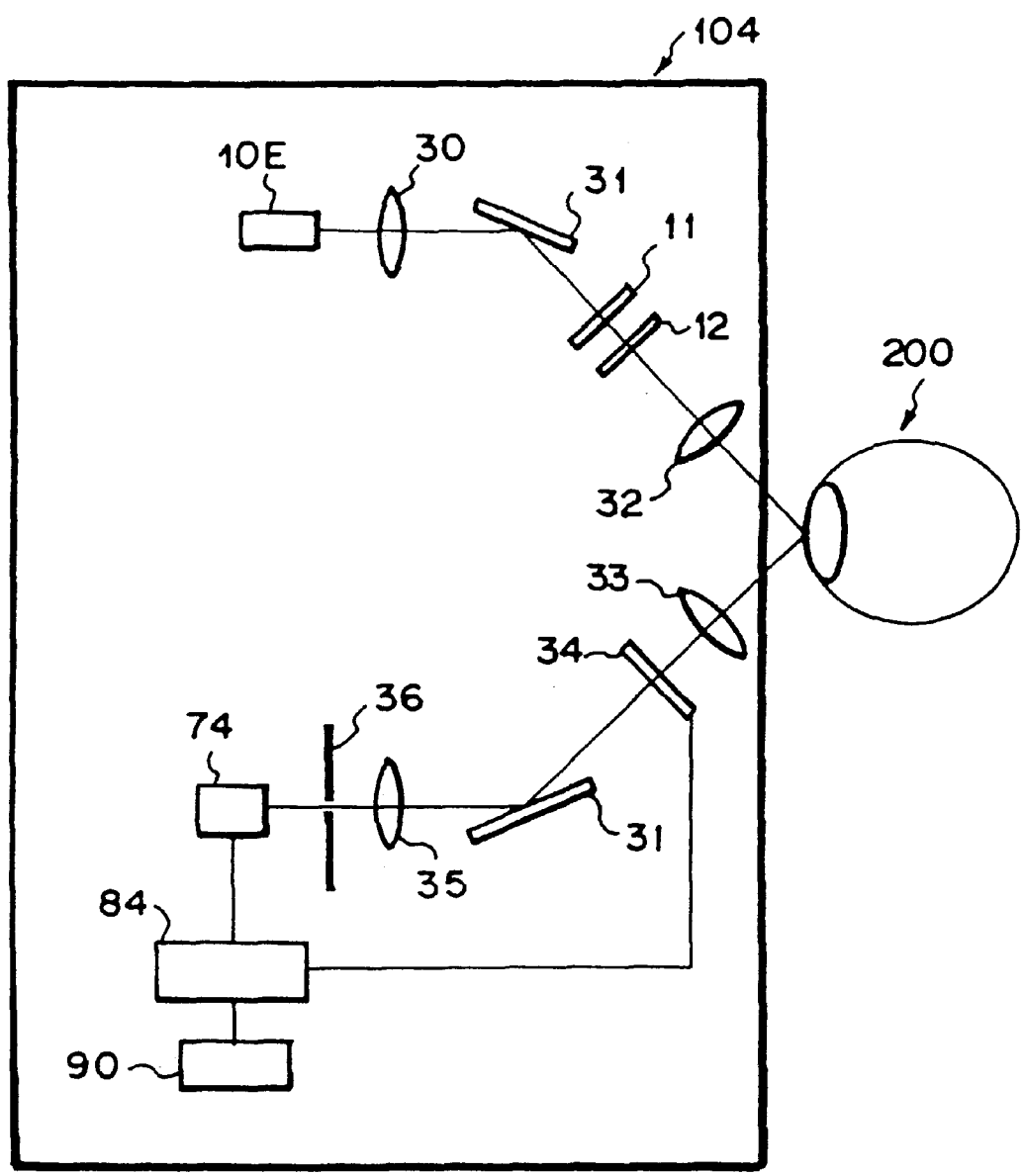
FIG. 15 is a schematic view showing an embodiment of the glucose concentration measuring apparatus for carrying out the sixth glucose concentration measuring method in accordance with the present invention.

FIG. 15 is a schematic view showing an embodiment of the glucose concentration measuring apparatus for carrying out the sixth glucose concentration measuring method in accordance with the present invention.

With reference to FIG. 15, a glucose concentration measuring apparatus 104 comprises a laser beam source 10E for radiating out a laser beam, and a lens 30 for collimating the laser beam having been radiated out of the laser beam source 10E. The glucose concentration measuring apparatus 104 also comprises a mirror 31 for reflecting the collimated laser beam at a predetermined angle, and the half-wave plate 11 for converting the reflected laser beam into a linearly polarized light beam. The glucose concentration measuring apparatus 104 further comprises the quarter-wave plate 12 for converting the linearly polarized light beam into a circularly polarized light beam, and a lens 32 for causing the circularly polarized light beam to impinge upon the interface $R_2$ between the cornea 210 and the anterior aqueous chamber 220 of the eyeball 200 at a predetermined angle of incidence and as an elliptically polarized light beam. The glucose concentration measuring apparatus 104 still further comprises an analyzer 34 and a photodetector 74 for detecting an azimuth angle and an amplitude of the elliptic polarization of the backward scattered light beam, which has been reflected from the interface $R_2$. The glucose concentration measuring apparatus 104 also comprises a mirror 31 for reflecting the backward scattered light beam, which has passed through the analyzer 34, at a predetermined angle. The glucose concentration measuring apparatus 104 further comprises converging lenses 33, 35 and a pinhole plate 36 having a pinhole, which constitute a confocal optical system for spatially separating only the backward scattered light beam, which comes from the interface $R_2$ between the cornea 210 and the anterior aqueous chamber 220, from the reflected light beams (backward scattered light beams) coming from the interfaces in the eyeball 200. The glucose concentration measuring apparatus 104 still further comprises a signal processing circuit 84 for calculating the refractive index $n_2$ of the aqueous humor, which fills the anterior aqueous chamber 220 of the eyeball 200, from the elliptically polarized state (the azimuth angle and the ellipticity of the elliptic polarization) of the backward scattered light beam, which comes from the interface $R_2$, and the angle of incidence of the circularly polarized light beam. The signal processing circuit 84 also calculates the concentration G of glucose in the aqueous humor in accordance with the calculated refractive index $n_2$ of the aqueous humor and the correlation between the refractive index $n_2$ of the aqueous humor and the concentration G of glucose in the aqueous humor, which correlation has been stored in the signal processing circuit 84. The glucose concentration measuring apparatus 104 also comprises the display device 90 for displaying the calculated concentration G of glucose in the aqueous humor.

The signal processing circuit 84 has the functions for the refractive index calculating means, the glucose concentration calculating means, and the storage section.

Specifically, with the technique for calculating the refractive index $n_2$ of the aqueous humor in accordance with the elliptically polarized state of the backward scattered light beam, an amplitude ratio $\psi$ and a phase difference $\Delta$ are obtained from ellipticity $\rho$ and an azimuth angle $\phi$ of the elliptic polarization, which have been detected by the analyzer 34 and the photodetector 74. From the obtained factors and the known angle of incidence $\psi_0$ upon the eyeball, the refractive index n is calculated with formula shown below.

$$n^2 = \sin^2\psi_0[1+\{\tan^2\psi_0(\cos^2 2\psi - \sin^2 2\psi \sin^2\Delta)\}/(1+\sin 2\psi \cos\Delta)^2]$$

The processing for calculating the refractive index $n_2$ in accordance with the state of elliptic polarization utilizes the principle of refractive index detection processing with an ellipsometer.

How the glucose concentration measuring apparatus 104 of FIG. 15 operates will be described hereinbelow.

Firstly, the laser beam is radiated out of the laser beam source 10E. The laser beam is collimated by the lens 30. Thereafter, the collimated laser beam is reflected at the predetermined angle from the mirror 31 and converted into the linearly polarized light beam by the half-wave plate 11. The linearly polarized light beam passes through the quarter-wave plate 12 and is thereby converted into the circularly polarized light beam. The circularly polarized light beam is caused by the lens 32 to impinge at the predetermined angle of incidence upon the interface $R_2$ between the cornea 210 and the anterior aqueous chamber 220 of the eyeball 200.

At this time, instead of being irradiated from the front of the eyeball 200, the circularly polarized light beam is irradiated at the predetermined angle of inclination to the eyeball 200. Therefore, at the interface $R_2$, the light beam impinges as the elliptically polarized light beam.

The circularly polarized light beam, which has been irradiated to the eyeball 200, is reflected as the backward scattered light beams from the interface $R_1$ and the interface $R_2$ in the eyeball 200. Of the backward scattered light beams, only the backward scattered light beam, which comes from the interface $R_2$, is allowed to pass through the pinhole of the pinhole plate 36 by the effects of the confocal optical system, which is constituted of the converging lenses 33 and 35.

The analyzer 34, which is located between the converging lens 33 and the converging lens 35, is adjusted such that the intensity of the light beam, which has passed through the pinhole of the pinhole plate 36 and is detected by the photodetector 74, (i.e, the intensity of the backward scattered light beam coming from the interface $R_2$) may become the highest. In accordance with the azimuth of the analyzer 34 and the output of the photodetector 74 obtained at this time, the azimuth angle $\phi$ and the ellipticity $\rho$ of the backward scattered light beam are calculated by the signal processing circuit 84.

The signal processing circuit 84 calculates the refractive index $n_2$ of the aqueous humor, which fills the anterior aqueous chamber 220 of the eyeball 200, from the ellipticity $\rho$ and the azimuth angle $\phi$, which have been calculated, and the angle of incidence of the circularly polarized light beam upon the eyeball 200.

The signal processing circuit 84 also calculates the concentration G of glucose in the aqueous humor in accordance with the calculated refractive index $n_2$ of the aqueous humor and the correlation between the refractive index $n_2$ of the aqueous humor and the concentration G of glucose in the aqueous humor, which correlation has been stored in the signal processing circuit 84. The calculated concentration G of glucose in the aqueous humor is displayed on the display device 90.

In this manner, with the glucose concentration measuring apparatus 104 of FIG. 15, the technique for the separate detection in the spatial domain with the confocal optical system is employed, in which the difference in optical path length between the first backward scattered light beam and the second backward scattered light beam is utilized, the difference occurring due to the difference between the positions of occurrence of the first and second backward scattered light beams. Also, the refractive index of the aqueous humor (the refractive index of the aqueous humor in the vicinity of the interface with the cornea) is be calculated in accordance with the polarized state of the elliptically polarized light beam. The concentration of glucose in the aqueous humor can then be determined non-invasively and with a high accuracy in accordance with the correspondence relationship between the refractive index of the aqueous humor and the concentration of glucose in the aqueous humor, which relationship has been found previously, and in accordance with the calculated refractive index of the aqueous humor. Also, the concentration of glucose in the aqueous humor can be measured non-invasively and with the constitution simpler than with the conventional techniques.

With the conventional technique wherein the concentration of glucose is measured by measuring the absorbance of the aqueous humor, such that measurement error due to the presence of many kinds of constituents, which absorb the incident light beam, in the aqueous humor, it is necessary for the measurement to be repeated by using a plurality of kinds (ordinarily, at least five kinds) of light beams having different wavelengths. However, with this embodiment of the glucose concentration measuring apparatus 104 in accordance with the present invention, wherein the correspondence relationship between the refractive index with respect to one kind of light beam having a predetermined wavelength and the concentration of glucose is utilized, the measurement can be carried out by using only the light beam having the predetermined wavelength, and the time required to carry out the measurement can be kept markedly short.

What is claimed is:

1. A glucose concentration measuring method, comprising the steps of:
   i) irradiating a light beam from a predetermined light source to an eyeball of a subject that is located at a predetermined position;
   ii) detecting intensities of first and second backward scattered lights of said light beam, wherein said first backward scattered light is from an interface between a cornea of said eyeball and ambient air, and said second backward scattered light is from an interface between said cornea and an anterior aqueous chamber of said eyeball;
   iii) calculating a refractive index of an aqueous humor from said intensities of said first and second backward scattered lights; and
   iv) calculating a concentration of glucose in said aqueous humor in accordance with a correlation between a predetermined refractive index of said aqueous humor and concentration of glucose in said aqueous humor, and in accordance with said calculated refractive index of said aqueous humor.

2. A glucose concentration measuring method, comprising the steps of:
   i) splitting a low coherence light beam from a predetermined light source into a signal light beam and a reference light beam, each of which travels along or one of two different optical paths;
   ii) modulating at least one of said signal light beam and said reference light beam, wherein a slight difference in frequency occurs between them;
   iii) irradiating said signal light beam to an eyeball of a subject that is located at a predetermined position;
   iv) producing a first backward scattered light of said signal light beam, wherein said first backward scattered light is from an interface between a cornea of said eyeball and ambient air, and said reference light beam interferes with said first backward scattered light by adjusting an optical path length of said reference light beam to create a first interference light beam;
   v) measuring an intensity of said first interference light beam;
   vi) calculating an intensity of said first backward scattered light from said intensity of said first interference light beam;
   vii) producing a second backward scattered light of said signal light beam, said second backward scattered light is from an interface between an anterior aqueous chamber and said cornea of said eyeball, and said reference light beam interferes with said second backward scattered light by adjusting said optical path length of said reference light beam to create a second interference light beam;
   viii) measuring an intensity of said second interference light beam;
   ix) calculating an intensity of said second backward scattered light from said intensity of said second interference light beam;
   x) calculating a refractive index of an aqueous humor from said intensities of said first and second backward scattered lights; and
   xi) calculating a concentration of glucose in said aqueous humor in accordance with a correlation between a predetermined refractive index of said aqueous humor and concentration of glucose in said aqueous humor, and in accordance with said calculated refractive index of said aqueous humor.

3. A glucose concentration measuring method, comprising the steps of:
   i) splitting a coherent light beam from a predetermined light source, the frequency of which is swept temporally in a sawtooth-like form, into a signal light beam and a reference light beam, each of which travels along one of two different optical paths;
   ii) irradiating said signal light beam to an eyeball of a subject that is located at a predetermined position;
   iii) producing a first backward scattered light of said signal light beam, wherein said first backward scattered light is from an interface between a cornea of said eyeball and ambient air, and said reference light beam interferes with said first backward scattered light and includes said coherent light beam, which has been radiated out of said light source with a difference in time in accordance with a difference between an optical path length of said signal light beam and said first backward scattered light and an optical path length of said reference light beam, and which has a difference in frequency with respect to said first backward scattered light, to create a first interference light beam;
   iv) measuring an intensity of said first interference light beam;
   v) calculating an intensity of said first backward scattered light from said intensity of said first interference light beam;
   vi) producing a second backward scattered light of said signal light, said second backward scattered light is from an interface between an anterior aqueous chamber and said cornea of said eyeball, and said reference light beam interferes with said first backward scattered light and includes said coherent light beam, which has been radiated out of said light ;source with a difference in time in accordance with a difference between an optical path length of said signal light beam and said second backward scattered light and an optical path length of said reference light beam, and which has a difference in frequency with respect to said second backward scattered light, to create a second interference light beam;

vii) measuring an intensity of said second interference light beam;

viii) calculating an intensity of said second backward scattered light from said intensity of said second interference light beam;

ix) calculating a refractive index of an aqueous humor from said intensities of said first and second backward scattered lights and x) calculating a concentration of glucose in said aqueous humor in accordance with a correlation between a predetermined refractive index of said aqueous humor and concentration of glucose in said aqueous humor, and in accordance with said calculated refractive index of said aqueous humor.

4. A glucose concentration measuring method, comprising the steps of:

i) irradiating an ultrashort pulsed light beam from a predetermined light source to an eyeball of a subject;

ii) measuring intensities of first and second backward scattered lights of said ultrashort pulsed light beam by temporally separating said first and second backward scattered lights from each other, wherein said first backward scattered light is from an interface between a cornea of said eyeball and ambient air, and said second backward scattered light is from an interface between an anterior aqueous chamber and said cornea of said eyeball;

iii) calculating a refractive index of an aqueous humor from said intensities of said first and second backward scattered lights; and iv) calculating a concentration of glucose in said aqueous humor in accordance with a correlation between a predetermined refractive index of said aqueous humor and concentration of glucose in said aqueous humor, and in accordance with said calculated refractive index of said aqueous humor.

5. A glucose concentration measuring method, comprising the steps of:

i) irradiating a light beam from a predetermined light source to an eyeball of a subject that is located at a predetermined position;

ii) detecting intensities of first and second backward scattered lights of said light beam, wherein said first backward scattered light is from an interface between a cornea of said eyeball and ambient air, and said second backward scattered light is from an interface between an anterior aqueous chamber and said cornea of said eyeball, said intensities are detected at a position that is conjugate with the corresponding interface by use of a confocal optical system, in which one of focusing points is set at each of said interfaces;

iii) calculating a refractive index of an aqueous humor from said intensities of said first and second backward scattered lights and iv) calculating a concentration of glucose in said aqueous humor in accordance with a correlation between a predetermined refractive index of said aqueous humor and concentration of glucose in said aqueous humor, and in accordance with said calculated refractive index of said aqueous humor.

6. A method as defined in any one of claims 1, 2, 3, 4, or 5, wherein a refractive index n1 of said cornea is calculated with the formula:

$$I_{R1}=I_0\{(n_0-n_1)/(n_0+n_1)\}^2$$

where $I_0$ represents the intensity of said light beam impinging upon said eyeball, $I_{R1}$ represents the intensity of said first backward scattered light, and $n_0$ represents the refractive index of said ambient air; and a refractive index $n_2$ of said aqueous humor is calculated with the formula:

$$I_{R2}=I_0(1-R1)^2 10^{-2ad}\{(n_1-n_2)/(n_1+n_2)\}^2$$

where $\{(n_0-n_1)/(n_0+n_1)\}^2=R1$, $I_{R2}$ represents the intensity of said second backward scattered light, a represents the absorbance of said cornea, and d represents the thickness of said cornea.

7. A method as defined in any one of claims 1, 2, 3, 4, or 5, wherein, with the same operation as that for the detection of said intensities of said first and second backward scattered light beam, said light beam having been radiated out of said light source is irradiated to a standard reflecting plate with a predefined reflectivity instead of said eyeball, wherein an intensity Is of said light beam having been reflected from said standard reflecting plate is detected, a reflectivity R1 of said interface between said ambient air and said cornea and a reflectivity R2 of said interface between said cornea and said anterior aqueous chamber are calculated in accordance with the detected intensity Is, a detected intensity $I_{R1}$ of said first backward scattered light, a detected intensity $I_{R2}$ of said second backward scattered light, and a reflectivity Rs of said standard reflecting plate, the calculations of said reflectivities R1 and R2 are defined with the formulas:

$$R1 = Rs \times I_{R1}/Is$$

$$R2 = Rs \times I_{R2}/Is$$

a refractive index n1 of said cornea and a refractive index n0 of said ambient air is calculated from the calculated reflectivity R1 with the formula:

$$R1=\{(n_0-n_1)/(n_0+n_1)\}^2$$

and a refractive index n2 of said aqueous humor and the calculated refractive index n1 of said cornea is calculated from the calculated reflectivity R2 with the formula:

$$R2=\{(n_1-n_2)/(n_1+n_2)\}^2$$

8. A method as defined in any one of claims 1, 2, 3, 4, or 5, wherein said refractive index of said aqueous humor is corrected in accordance with a temperature of said aqueous humor.

9. A method as defined in claim 8, wherein a first temperature, which is selected from a group consisting of a surface temperature of said cornea, a skin temperature in a vicinity of said cornea, and an ambient air temperature in a vicinity of said cornea, is measured; and said temperature of said aqueous humor is determined from a predetermined intra-eyeball temperature distribution in accordance with said first temperature.

10. A method as defined in claim 9, wherein said surface temperature of said cornea is measured by measuring infrared rays radiated out of the surface of said cornea.

11. A method as defined in claim 8, wherein a first temperature, which is selected from a group consisting of a surface temperature of said cornea, a skin temperature in a vicinity of said cornea, and an ambient air temperature in a vicinity of said cornea, is measured;

an intra-eyeball temperature distribution in accordance with said first temperature is determined; and said temperature of said aqueous humor is determined from said intra-eyeball temperature distribution.

12. A method as defined in claim 11, wherein said surface temperature of said cornea is measured by measuring infrared rays radiated out of the surface of said cornea.

13. A method as defined in claim 8, wherein a first temperature, which is selected from a group consisting of a surface temperature of said cornea, a skin temperature in a vicinity of a cornea, and an ambient air temperature in a vicinity of said cornea, is measured;

a deep portion temperature of said anterior aqueous chamber is measured; and said temperature of said aqueous humor is determined from a predetermined intra-eyeball temperature distribution in accordance with said first temperature and said deep portion temperature.

14. A method as defined in claim 13, wherein said deep portion temperature of said anterior aqueous chamber is measured by measuring infrared rays radiated out of a deep portion in an external auditory miatus.

15. A method as defined in claim 14, wherein said surface temperature of said cornea is measured by measuring infrared rays radiated out of the surface of said cornea.

16. A method as defined in claim 13, wherein said surface temperature of said cornea is measured by measuring infrared rays radiated out of the surface of said cornea.

17. A method as defined in claim 8, wherein a first temperature, which is selected from a group consisting of a surface temperature of said cornea, a skin temperature in a vicinity of said cornea, and an ambient air temperature in a vicinity of said cornea, is measured;

a deep portion temperature of said anterior aqueous chamber is measured;

an intra-eyeball temperature distribution in accordance with said first temperature and said deep portion temperature is determined; and said temperature of said aqueous humor is determined from said intra-eyeball temperature distribution.

18. A method as defined in claim 17, wherein deep portion temperature of said anterior aqueous chamber is measured by measuring infrared rays radiated out of a deep portion in an external auditory miatus.

19. A method as defined in claim 18, wherein said surface temperature of said cornea is measured by measuring infrared rays radiated out of the surface of said cornea.

20. A method as defined in claim 17, wherein said surface temperature of said cornea is measured by measuring infrared rays radiated out of the surface of said cornea.

21. A method as defined in claim 8, wherein a temperature distribution of said cornea is determined in accordance with an intra-eyeball temperature distribution, and a correction is made for at least one of a refractive index and an absorbance of said cornea in accordance with said temperature distribution of said cornea.

22. A glucose concentration measuring method, comprising the steps of:

i) irradiating a circularly polarized light beam from a predetermined light source to an eyeball of a subject that is located at a predetermined position, wherein said circularly polarized light beam impinges said eyeball at a predetermined angle of incidence;

ii) detecting an elliptically polarized state of backward scattered light of said circularly polarized light beam, wherein said backward scattered light is from an interface between an anterior aqueous chamber and a cornea of said eyeball, the elliptically polarized state being detected at a position that is conjugate with said interface by use of a confocal optical system;

iii) calculating a refractive index of an aqueous humor in accordance with said elliptically polarized state of said backward scattered light; and iv) calculating a concentration of glucose in said aqueous humor in accordance with a correlation between a predetermined refractive index of said aqueous humor and concentration of glucose in said aqueous humor, and in accordance with said calculated refractive index of said aqueous humor.

23. A method as defined in any one of claims 1, 2, 3, 4, 5, or 22, wherein said light source is a semiconductor laser; and an ND filter is located in an optical path of a laser beam that has been radiated out of said semiconductor laser, wherein said ND filter is inclined with respect to a plane that is normal to a direction of travel of said laser beam to obstruct return light from impinging upon said semiconductor laser.

24. A method as defined in any one of claims 1, 2, 3, 4, 5, or 22, wherein a correlation between the refractive index of said aqueous humor and said concentration of glucose in said aqueous humor is represented by the formula:

$$n=1.3332\ 2+1.6\times10^{-6}\times G$$

where n represents said refractive index of said aqueous humor, and G represents said concentration of glucose (in mg/dl).

25. A glucose concentration measuring apparatus, comprising:

i) a light source for irradiating a light beam to an eyeball of a subject that is located at a predetermined position;

ii) a photodetector for detecting intensities of first and second backward scattered lights of said light beam, wherein said first backward scattered light is from an interface between a cornea of said eyeball and ambient air, and said second backward scattered light is from an interface between said cornea and an anterior aqueous chamber of said eyeball;

iii) a refractive index calculating means for calculating a refractive index of said aqueous humor from said intensities of said first and second backward scattered lights;

iv) a storage section operable to store predetermined information representing a correspondence relationship between said refractive index of said aqueous humor and a concentration of glucose in said aqueous humor; and v) a glucose concentration calculating means for calculating a concentration of glucose in said aqueous humor in accordance with the stored correspondence relationship and the calculated refractive index of the aqueous humor.

26. A glucose concentration measuring apparatus, comprising:

i) a light source device for radiating out a low coherence light beam to an eyeball of a subject;

ii) an optical path splitting means for splitting said low coherence light beam into a signal light beam and a reference light beam, each of which travels along one of two different optical paths;

iii) a modulation means, located in at least one of the two different optical paths, for modulating at least one of said signal light beam and said reference light beam, wherein a slight difference in frequency occurs between them;

iv) an optical path length adjusting means for adjusting a length of said optical path which said reference light beam travels v) a wavefront matching means for:
matching a wave front of a first backward scattered light of said signal light and a wave front of said reference light beam with each other, wherein said first backward scattered light is from an interface between a cornea of said eyeball and ambient air; and matching a wave front of a second backward scattered light of said signal light and a wave front of said reference light beam with each other, said second backward scattered light is from an interface between an anterior aqueous chamber and said cornea of said eyeball;

vi) a photodetector for photoelectrically detecting an intensity of a first interference light beam, which is obtained from the matching of said wave front of said first backward scattered light and said wave front of said reference light beam with each other, and an intensity of a second interference light beam, which is obtained from the matching of wave front of said second backward scattered light and said wave front of said reference light beam with each other;

vii) a heterodyne operation means for calculating intensities of said first and second backward scattered lights from said intensity of said first and second interference light beams, respectively:

viii) a refractive index calculating means for calculating a refractive index of an aqueous humor from said intensities of said first and second backward scattered lights;

ix) a storage section operable to store predetermined information representing a correspondence relationship between said refractive index of said aqueous humor and a concentration of glucose in said aqueous humor; and x) a glucose concentration calculating means for calculating a concentration of glucose in said aqueous humor in accordance with the stored correspondence relationship and the calculated refractive.

27. A glucose concentration measuring apparatus, comprising:

i) a light source device for radiating out a coherent light beam, the frequency of which is swept temporally in a sawtooth-like form;

ii) an optical path splitting means for splitting said coherent light beam into a signal light beam irradiated to an eyeball of a subject and a reference light beam, each of which travels along one of two different optical paths;

iii) a wavefront matching means for:
matching a wave front of a first backward scattered light of said signal light beam and a wave front of said reference light beam with each other, wherein said first backward scattered light is from an interface between a cornea of said eyeball and ambient air, and said reference light beam includes said coherent light beam, which has been radiated out of said light source device with a difference in time in accordance with a difference between an optical path length of said signal light beam and said first backward scattered light and an optical path length of said reference light beam, and which has a difference in frequency with respect to said first backward scattered light beam; and matching a wave front of a second backward scattered light of said signal light beam and a wave front of said reference light beam with each other, said second backward scattered light is from an interface between an anterior aqueous chamber and said cornea of said eyeball, and said reference light beam includes said coherent light beam, which has been radiated out of said light source device with a difference in time in accordance with a difference between said optical path length of said signal light beam and said second backward scattered light and said optical path length of said reference light beam, and which has a difference in frequency with respect to said second backward scattered light;

iv) a photodetector for photoelectrically detecting an intensity of a first interference light beam, which is obtained from the matching of said wave front of said first backward scattered light and said wave front of said reference light beam, said reference light beam having a slight difference in frequency with respect to said first backward scattered light, and an intensity of a second interference light beam, which is obtained from the matching of said wave front of said second backward scattered light and said wave front of said reference light beam, said reference light beam having a slight difference in frequency with respect to said second backward scattered light;

v) a heterodyne operation means for calculating an intensity of said first backward scattered light from said intensity of said first interference light beam, and calculating an intensity of said second backward scattered light from said intensity of said second interference light beam;

vi) a refractive index calculating means for calculating a refractive index of said aqueous humor from said intensity of said first backward scattered light and said intensity of said second backward scattered light;

vii) a storage section operable to store predetermined information representing a correspondence relationship between said refractive index of said aqueous humor and a concentration of glucose in said aqueous humor; and viii) a glucose concentration calculating means for calculating a concentration of glucose in said aqueous humor in accordance with the stored correspondence relationship and the calculated refractive index of the aqueous humor.

28. A glucose concentration measuring apparatus, comprising:

i) a light source device for radiating out an ultrashort pulsed light beam;

ii) an optical time-domain backward scattering measurement means for irradiating said ultrashort pulsed light beam to an eyeball of a subject, and carrying out a time series measurement of intensities of first and second backward scattered lights of said ultrashort pulsed light beam, wherein said first backward scattered light is from an interface between a cornea of said eyeball and ambient air, and said second backward scattered light is from an interface between an anterior aquecus chamber and said cornea of said eyeball;

iii) a refractive index calculating means for calculating a refractive index of an aqueous humor from said intensity of said first backward scattered light and said intensity of said second backward scattered light;

iv) a storage section operable to store predetermined information representing a correspondence relationship between said refractive index of said aqueous humor and a concentration of glucose in said aqueous humor; and v) a glucose concentration calculating means for calculating a concentration of glucose in said aqueous humor in accordance with the stored correspondence relationship and the calculated refractive index of the aqueous humor.

29. A glucose concentration measuring apparatus, comprising:

i) a light source device for irradiating a light beam to an eyeball of a subject that is located at a predetermined position;

ii) a confocal optical system for spatially separating first and second backward scattered lights of said light beam, wherein said first backward scattered light is from an interface between a cornea of said eyeball and ambient air, and said second backward scattered light is from an interface between an anterior aqueous chamber and said cornea of said eyeball;

iii) a photodetector for detecting intensities of said first and second backward scattered lights that have been spatially separated from each other;

iv) a refractive index calculating means for calculating a refractive index of said aqueous humor from said intensities of said first and second backward scattered lights;

v) a storage section operable to store predetermined information representing a correspondence relationship between said refractive index of said aqueous humor and a concentration of glucose in said aqueous humor; and vi) a glucose concentration calculating means for calculating a concentration of glucose in said aqueous humor in accordance with the stored correspondence relationship and the calculated refractive index of the aqueous humor.

30. An apparatus as defined in any one of claims 25, 26, 27, 28, or 29, wherein said refractive index calculating means calculates a refractive index n1 of said cornea with the formula:

$$I_{R1}=I_0\{(n_0-n_1)/(n_0+n_1)\}^2$$

where $I_0$ represents the intensity of said light beam impinging upon said eyeball, $I_{R1}$ represents the intensity of said first backward scattered light, and n0 represents the refractive index of said ambient air, and said refractive index calculating means calculates a refractive index n2 of said aqueous humor with the formula:

$$I_{R2}=I_0(1-R11)^2 10^{-2ad}\{(n_1-n_2)/(n_1+n_2)\}^2$$

where $\{(n_0-n_1)/(n_0+n_1)\}^2=R1$, $I_{R2}$ represents the intensity of said second backward scattered light, a represents the absorbance of said cornea, and d represents the thickness of said cornea.

31. An apparatus as defined in any one of claims 25, 26, 27, 28, or 29, wherein a standard reflecting plate with a predefined reflectivity is located to be inserted into and retreated from an optical path of said light beam in front of said eyeball;

said refractive index calculating means calculates a reflectivity R1 of said interface between said ambient air and said cornea and a reflectivity R2 of said interface between said cornea and said anterior aqueous chamber in accordance with an intensity Is of said light beam having been reflected from said standard reflecting plate, which intensity is detected by said photodetector, a detected intensity $I_{R1}$ of said first backward scattered light, a detected intensity $I_{R2}$ of said second backward scattered light, and a reflectivity Rs of said standard reflecting plate, the calculations of said reflectivities R1 and R2 are defined with the formulas:

$$R1=Rs\times I_{R1}/Is$$

$$R2=Rs\times I_{R2}/Is$$

said refractive index calculating means calculates a refractive index $n_1$ of said cornea and a refractive index $n_0$ of said ambient air from the calculated reflectivity R1 with the formula:

$$R1=\{(n_0-n_1)/(n_0+n_1)\}^2$$

and said refractive index calculating means calculates a refractive index $n_2$ of aqueous humor and the calculated refractive index $n_1$ of said cornea from the calculated reflectivity R2 with the formula:

$$R2=\{(n_1-n_2)/(n_1-n_2)\}^2$$

32. An apparatus as defined in any one of claims 25, 26, 27, 28, or 29, further comprising an aqueous humor refractive index correcting means for correcting said refractive index of said aqueous humor in accordance with a temperature of said aqueous humor.

33. An apparatus as defined in claim 32, wherein said aqueous humor refractive index correcting means comprises:

an outer surface temperature detecting means for measuring a first temperature, which is selected from a group consisting of a surface temperature of said cornea, a skin temperature in a vicinity of said cornea, and an ambient air temperature in a vicinity of said cornea;

a predetermined intra-eyeball temperature distribution table in accordance with said first temperature; and an aqueous humor temperature determining means for determining said temperature of said aqueous humor by making reference to said intra-eyeball temperature distribution table and in accordance with said first temperature.

34. An apparatus as defined in claim 33, wherein said outer surface temperature detecting means is an infrared measuring means for measuring infrared rays radiated out of a surface of said cornea.

35. An apparatus as defined in claim 32, wherein said aqueous humor refractive index correcting means comprises:

an outer surface temperature detecting means for measuring a first temperature, which is selected from a group consisting of a surface temperature of said cornea, a skin temperature in a vicinity of said cornea, and an ambient air temperature in a vicinity of said cornea;

an intra-eyeball temperature distribution determining means for determining an intra-eyeball temperature distribution in accordance with said first temperature; and an aqueous humor temperature determining means for determining said temperature of said aqueous humor from said intra-eyeball temperature distribution.

36. An apparatus as defined in claim 35, wherein said outer surface temperature detecting means is an infrared measuring means for measuring infrared rays radiated out of a surface of said cornea.

37. An apparatus as defined in claim 32, wherein said aqueous humor refractive index correcting means comprises:

an outer surface temperature detecting means for measuring a first temperature, which is selected from a group consisting of a surface temperature of said cornea, a skin temperature in a vicinity of said cornea, and an ambient air temperature in a vicinity of said cornea;

a deep portion temperature detecting means for measuring a deep portion temperature of said anterior aqueous chamber;

a predetermined intra-eyeball temperature distribution table set in accordance with said first temperature; and an aqueous humor temperature determining means for determining said temperature of said aqueous humor by making reference to said intra-eyeball temperature distribution table.

38. An apparatus as defined in claim 37, wherein said deep portion temperature detecting means is an infrared measuring means for measuring infrared rays radiated out of a deep portion in an external auditory miatus.

39. An apparatus as defined in claim 38, wherein said outer surface temperature detecting means is an infrared measuring means for measuring infrared rays radiated out of a surface of said cornea.

40. An apparatus as defined in claim 37, wherein said outer surface temperature detecting means is an infrared measuring means for measuring infrared rays radiated out of a surface of said cornea.

41. An apparatus as defined in claim 32, wherein said aqueous humor refractive index correcting means comprises:

an outer surface temperature detecting means for measuring a first temperature, which is selected from a group consisting of a surface temperature of said cornea, a skin temperature in a vicinity of said cornea, and an ambient air temperature in a vicinity of said cornea;

a deed portion temperature detecting means for measuring a deep portion temperature of said anterior aqueous chamber;

an intra-eyeball temperature distribution determining means for determining an intra-eyeball temperature distribution in accordance with said first temperature; and an aqueous humor temperature determining means for determining said temperature of said aqueous humor from said intra-eyeball temperature distribution.

42. An apparatus as defined in claim 41, wherein said deep portion temperature detecting means is an infrared measuring means for measuring infrared rays radiated out of a deep portion in an external auditory miatus.

43. An apparatus as defined in claim 42, wherein said outer surface temperature detecting means is an infrared measuring means for measuring infrared rays radiated out of a surface of said cornea.

44. An apparatus as defined in claim 41, wherein said outer surface temperature detecting means is an infrared measuring means for measuring infrared rays radiated out of a surface of said cornea.

45. An apparatus as defined in claim 32, further comprising a cornea optical characteristics correcting means for determining a temperature distribution of said cornea in accordance with an intra-eyeball temperature distribution, and making a correction for at least one of a refractive index and an absorbance of said cornea and in accordance with said temperature distribution of said cornea.

46. A glucose concentration measuring apparatus, comprising:

i) a light source device for irradiating a circularly polarized light beam to an eyeball of a subject that is located at a predetermined position, wherein said circularly polarized light beam impinges upon said eyeball at a predetermined angle of incidence;

ii) a confocal optical system for extracting a backward scattered light of said circularly polarized light beam, wherein said backward scattered light is from an interface between an anterior aqueous chamber and a cornea of said eyeball;

iii) an elliptically polarized state detecting means for detecting an elliptically polarized state of the extracted backward scattered light;

iv) a refractive index calculating means for calculating a refractive index of an aqueous humor in accordance with said elliptically polarized state of said backward scattered light;

v) a storage section operable to store predetermined information representing a correspondence relationship between said refractive index of said aqueous humor and a concentration of glucose in said aqueous humor; and vi) a glucose concentration calculating means for calculating a concentration of glucose in said aqueous humor in accordance with the stored correspondence relationship and the calculated refractive index of the aqueous humor.

47. An apparatus as defined in any one of claims 25, 26, 27, 28, 29, or 46, wherein said light source device is a semiconductor laser; and an ND filter is located in an optical path of a laser beam that has been radiated out of said semiconductor laser, wherein said ND filter is inclined with respect to a plane that is normal to a direction of travel of said laser beam to obstruct return light from impinging upon said semiconductor laser.

48. An apparatus as defined in any one of claims 25, 26, 27, 28, 29, or 46, wherein a correlation, which is stored in said storage section, is represented by the formula:

$$n=1.33322+1.6\times10^{-6}\times G$$

where n represents said refractive index of said aqueous humor, and G represents said concentration of glucose (in mg/dl).

* * * * *